US012674026B2

(12) United States Patent
Lochmann et al.

(10) Patent No.: US 12,674,026 B2
(45) Date of Patent: Jul. 7, 2026

(54) PROCESS FOR PREPARING POLYOL-BASED ESTERS OF ACYL-CAPPED HYDROXY CARBOXYLIC ACIDS

(71) Applicant: KetoLipix Therapeutics GmbH, Hamburg (DE)

(72) Inventors: Dirk Lochmann, Witten (DE); Sebastian Reyer, Witten (DE); Michael Stehr, Witten (DE)

(73) Assignee: KetoLipix Therapeutics GmbH (DE)

( * ) Notice: Subject to any disclaimer, the term of this patent is extended or adjusted under 35 U.S.C. 154(b) by 1225 days.

(21) Appl. No.: 17/618,591

(22) PCT Filed: Jun. 12, 2019

(86) PCT No.: PCT/EP2019/065278

§ 371 (c)(1),
(2) Date: Dec. 13, 2021

(87) PCT Pub. No.: WO2020/249198

PCT Pub. Date: Dec. 17, 2020

(65) Prior Publication Data

US 2025/0197566 A1 Jun. 19, 2025

(51) Int. Cl.
*C08G 65/48* (2006.01)
*A61K 47/34* (2017.01)

(52) U.S. Cl.
CPC .............. *C08G 65/48* (2013.01); *A61K 47/34* (2013.01)

(58) Field of Classification Search
None
See application file for complete search history.

(56) References Cited

FOREIGN PATENT DOCUMENTS

WO WO-2013150153 A1 * 10/2013 ........... A61K 31/225

* cited by examiner

*Primary Examiner* — Sun Jae Yoo
(74) *Attorney, Agent, or Firm* — Edward E. Sowers; Brannon Sowers & Cracraft PC

(57) ABSTRACT

The invention relates to a method for producing polyol esters, especially polyglycerol esters, of acyl-capped or acyl-blocked 3-hydroxybutyric acid as well as the products thus obtained and to their functionalized (e. g. esterified) derivatives, as well as to the various uses and applications of these products.

9 Claims, No Drawings

PROCESS FOR PREPARING POLYOL-BASED ESTERS OF ACYL-CAPPED HYDROXY CARBOXYLIC ACIDS

CROSS-REFERENCES TO RELATED APPLICATIONS

This application is a National Stage filing of International Application PCT/EP 2019/065278 filed Jun. 12, 2019, entitled "METHOD FOR PRODUCING POLYOL-BASED ESTERS OF ACYL-CAPPED 3=HYDROXYCARBOXYLIC ACIDS". The subject application claims priority to PCT/EP 2019/065278 and incorporates all by reference herein, in its entirety.

BACKGROUND OF THE INVENTION

The present invention relates to the field of keto bodies and related metabolism and the therapy of related diseases.

Especially, the present invention relates to a method for producing polyol esters of acyl-capped (=acyl-blocked) 3-hydroxybutyric acid (synonymously also referred to as "3-hydroxybutanoic acid", "beta-hydroxybutyric acid", "beta-hydroxybutanoic acid" etc.), especially polyglycerol esters of acyl-capped (acyl-blocked) 3-hydroxybutyric acid, as well as the reaction products thus obtainable or thus prepared (i. e. polyol esters of acyl-capped or acyl-blocked 3-hydroxybutyric acid, especially polyglycerol esters of acyl-capped or acyl-blocked 3-hydroxybutyric acid) and their functionalized (i. e. esterified) derivatives as well as their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i. e. polyol esters of acyl-capped or acyl-blocked 3-hydroxybutyric acid, especially polyglycerol esters of acyl-capped or acyl-blocked 3-hydroxybutyric acid) or their functionalized (i. e. esterified) derivatives obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i. e. polyol esters of acyl-capped or acyl-blocked 3-hydroxybutyric acid, especially polyglycerol esters of acyl-capped or acyl-blocked 3-hydroxybutyric acid) or their functionalized (i. e. esterified) derivatives obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetoacetate or 3-oxobutyrate) and acetone as well as 3-hydroxybutyric acid (hereinafter also synonymously referred to as beta-hydroxybutyric acid or BHB or 3-BHB) or its salt (i. e. 3-hydroxybutyrate or beta-hydroxybutyrate), the latter being the most important of the three aforementioned compounds. 3-Hydroxybutyric acid or its salt occurs physiologically as the (R)-enantiomer, i. e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect in addition, the plasma half-life of 3-hydroxybutyric acid and its salts is so short that even if several grams are taken, the ketosis lasts only for about three to four hours, i. e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i. e. the metabolic conversion of caproic, caprylic and capric acid (i. e. of saturated linear $C_6$-, $C_8$- and $C_{10}$-fatty acids) from the corresponding triglycerides is intended.

Basically, however, from a pharmaceutical and clinical point of view, 3-hydroxybutyric acid as well as acetoacetate as a physiological precursor of 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid as well as acetoacetate (and thus 3-hydroxybutryric acid or its salts, which are physiologically obtainable by reduction of acetoacetate).

| Indication | Therapeutic effect |
|---|---|
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e. g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts as well as to acetoacetate (and thus physiologically to 3-hydroxybutyric acid and its salts), especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid or their salts.

Such method should especially make the respective BHB precursors and/or BHB metabolites accessible in an efficient way, especially in larger quantities and without significant amounts of toxic by-products.

In a completely surprising way, the applicant has now discovered that polyol esters, especially polyglycerol esters, of acyl-capped (=acyl-blocked) 3-hydroxybutyric acid as well as their functionalized derivatives represent an efficient and physiologically effective or physiologically compatible precursor and/or metabolite for the keto bodies 3-hydroxybutyric acid and acetoacetate or for 3-hydroxybutyric acid produced reductively therefrom under physiological conditions or their salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing polyol esters, especially polyglycerol esters, of acyl-capped (=acyl-blocked) 3-hydroxybutyric acid (beta-hydroxybutyric acid, 3-hydroxybutanoic acid).

Moreover, the present invention relates—according to a second aspect of the present invention—to a method for producing functionalized, especially fatty acid functionalized, polyol esters, especially polyglycerol esters, of acyl-capped (=acyl-blocked) 3-hydroxybutyric acid (beta-hydroxybutyric acid, 3-hydroxybutanoic acid).

Furthermore, the present invention relates according to a third aspect of the present invention—to a reaction product obtainable according to the inventive method described herein or a polyol ester, especially polyglycerol ester, of acyl-capped (acyl-blocked) 3-hydroxybutyric acid (beta-hydroxybutyric acid, 3-hydroxybutanoic acid) or respective mixtures thereof.

Likewise, the present invention—according to a fourth aspect of the present invention—relates to a pharmaceutical composition, especially a drug or medicament.

Furthermore, the present invention—according to a fifth aspect of the present invention—relates to an inventive reaction product or an inventive polyol ester, especially polyglycerol ester, of acyl-capped (acyl-blocked) 3-hydroxybutyric acid (beta-hydroxybutyric acid, 3-hydroxybutanoic acid) or a respective mixture thereof for the prophylactic and/or therapeutic treatment or for use in the prophylactic and/or therapeutic treatment of diseases of the human or animal body.

Furthermore, the present invention—according to a sixth aspect of the present invention—relates to the use of an inventive reaction product or an inventive polyol ester, especially polyglycerol ester, of acyl-capped (acyl-blocked) 3-hydroxybutyric acid (beta-hydroxybutyric acid, 3-hydroxybutanoic acid) or a respective mixture thereof for the prophylactic and/or therapeutic treatment or for producing a medicament for the prophylactic and/or therapeutic treatment of diseases of the human or animal body.

Furthermore, the present invention—according to a seventh aspect of the present invention—relates to the use of an inventive reaction product or an inventive polyol ester, especially polyglycerol ester, of acyl-capped (acyl-blocked)

3-hydroxybutyric acid (beta-hydroxybutyric acid, 3-hydroxybutanoic acid) or a respective mixture thereof.

Furthermore, the present invention—according to an eighth aspect of the present invention—relates to a food and/or food product; further, especially special and/or advantageous embodiments of the food and/or food product according to the invention are similarly disclosed.

Finally, the present invention—according to an ninth aspect of the present invention—relates to the use of an inventive reaction product or an inventive polyol ester, especially polyglycerol ester, of acyl-capped (acyl-blocked) 3-hydroxybutyric acid (beta-hydroxybutyric acid, 3-hydroxybutanoic acid) or a respective mixture thereof in a food and/or a food product.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 1.00% or 100% by weight, respectively, including all components or ingredients, especially as defined below; however, this is self-evident for the person skilled in the art.

In addition, the skilled person may, if necessary, deviate from the following range specifications without leaving the scope of the present invention.

Additionally, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

Thus, it is an object of the present invention—according to a first aspect of the present invention—to provide a method for producing polyol esters, especially polyglycerol esters, of acyl-capped (acyl-blocked) 3-hydroxybutyric acid (beta-hydroxybutyric acid, 3-hydroxybutanoic acid), wherein at least one compound of the general formula (I)

$$CH_3—CH(OR_2)—CH_2—C(O)OR^1 \qquad (I)$$

wherein, in the general formula (I), the radical $R^1$ represents hydrogen or $C_1$-$C_4$-alkyl, especially $C_1$-$C_4$-alkyl, preferentially methyl or ethyl, preferably ethyl, and the radical $R^2$ represents a radical $CH_3—C(O)—CH_2—C(O)—$, is reacted with at least one polyol (II) comprising at least two, especially at least three, hydroxyl groups (OH-groups), especially polyglycerol, so that, as a reaction product, at least one acyl-capped (acyl-blocked) 3-hydroxybutyric acid polyol ester (III), especially 3-hydroxybutyric acid polyglycerol ester, is obtained.

The inventive method thus results in a polyol ester, especially a polyglycerol ester, of 3-hydroxybutyric acid capped or blocked in the 3-position (=hydroxyl group position) with an acyl group.

An acyl group is a functional group in organic chemistry with the general structure A-(C═O)—, wherein the radical A represents an organyl radical (e. g, alkyl, aryl or a heteroaromatic group etc.) or a hydrogen atom. The acyl group is formally derived from carboxylic acids, aldehydes and carboxylic acid chlorides in which an OH-group or a hydrogen atom or a chloride is substituted by a radical A, respectively. An acylation refers to the introduction of such acyl group.

In the case that (as in the case of the invention) the acylation takes place at a hydroxyl group (OH-group) (namely at the OH-group located in the 3-position of the 3-hydroxybutyric acid), overall, an acyloxy group is formed which has the general structure A-(C═O)—O— (“A” as defined hereinabove).

According to the invention, an acyl-capped (=acyl-blocked) 3-hydroxybutyric acid is thus a butyric acid acylated in the 3-position (i. e. in the hydroxyl group position) or a butanoic acid acyloxylated in the 3-position.

As stated above, the applicant has, quite surprisingly, discovered that the polyol esters, especially polyglycerol esters, of acyl-capped (=acyl-blocked) 3-hydroxybutyric acid (which may optionally also be functionalized, as described in detail hereinbelow) thus produced are efficient, since physiologically compatible precursors and/or metabolites of the free 3-hydroxybutyric acid or their salts or esters, which can also be used in larger quantities in pharmaceutical or clinical applications because they are physiologically compatible.

The above-mentioned optionally functionalized polyol esters, especially polyglycerol esters, of acyl-capped (=acyl-blocked) 3-hydroxybutyric acid, which are accessible for the first time in an efficient manner through the production method according to the invention, represent a physiologically and pharmacologically relevant alternative to free 3-hydroxybutyric acid or its salts or esters (and also to the further keto body “acetoacetate”).

The production of such compounds by means of conventional organic synthesis is complex and costly, since 3-hydroxybutyric acid has an increased tendency to polymerize and to undergo other undesirable side reactions (e. g, dehydration, decomposition, etc.). Within the scope of the present invention, it was possible for the first time to provide an efficiently working production method with which optionally functionalized polyol esters, especially polyglycerol esters, of acyl-capped (acyl-blocked) 3-hydroxybutyric acid can be produced without undesired side reactions, especially in a single step.

The inventive method thus makes it possible for the first time to provide non-toxic optionally functionalized polyol esters, especially polyglycerol esters, of acyl-capped (acyl-blocked) 3-hydroxybutyric acid from known, commercially available and above all physiologically harmless components or educts (starting compounds). The resulting optionally functionalized polyol esters, especially polyglycerol esters, of acyl-capped 3-hydroxybutyric acid can be broken down physiologically, especially in the stomach and/or intestine, and release or generate the target molecule “3-hydroxybutyric acid” or its salts (and also the keto body acetoacetate from the acylation, which again can be further physiologically converted or reduced to 3-hydroxybutyric acid) as active ingredient or active component.

In addition, the aforementioned optionally functionalized polyol esters, especially polyglycerol esters, of acyl-capped (acyl-blocked) 3-hydroxybutyric acid also have an acceptable taste to ensure compatibility even when administered orally in larger quantities over a longer period of time (e. g. administration of 50 g daily dose or more).

Similarly, the production method according to the invention makes it possible to provide the polyol esters, especially polyglycerol esters, of acyl-capped (acyl-blocked) 3-hydroxybutyric acid free from toxic impurities.

During physiological cleavage in the stomach and/or intestine, the optionally functionalized polyol esters, especially polyglycerol esters, of acyl-capped (acyl-blocked) 3-hydroxybutyric acid is cleaved into the keto compounds 3-hydroxybutyric acid and 3-oxobutyrate (acetoacetate or acetacetate), which can be further reduced by the body to 3-hydroxybutyrate. Due to the presence of both 3-oxobutyrate radicals and 3-hydroxybutyrate radicals or 3-hydroxybutyric acid, there is a different rate of availability or release of the active ingredient 3-hydroxybutyric acid. Consequently, the inventive reaction product exhibits a retard effect Overall, the optionally functionalized polyol esters, especially polyglycerol esters, of acyl-capped (acyl-blocked) 3-hydroxybutyric acid according to the invention thus exhibits two keto bodies with different rates of degradation.

There is also an additional or further retardation since the keto bodies are in the form of a polyol ester and thus to release the active ingredients 3-hydroxybutyric acid in the free form and acetoacetate cleavage from the polyol must also take place. Overall, the active ingredients 3-hydroxybutyric acid and acetoacetate are released from the optionally functionalized polyol esters, especially polyglycerol esters, of acyl-capped (acyl-blocked) 3-hydroxybutyric acid by a multi-stage degradation with a retardation effect.

In addition, with appropriate selection of the starting materials, the method can also be carried out enantioselectively. For example, according to the invention, the production method allows the biologically relevant form, i. e. the (R)-enantiomer, to be enriched or obtained as not to burden the renal system of patients when administered orally (i. e, elimination via the kidneys). In principle, however, it is also possible, and under certain conditions may be useful, to enrich or obtain the (S)-enantiomer.

The production method according to the invention usually results in a mixture of different polyol esters, especially polyglycerol esters, of acyl-capped (acyl-blocked) 3-hydroxybutyric acid, i. e. in a mixture of at least two, especially at least three different polyol esters, especially polyglycerol esters, of acyl-capped (acyl-blocked) 3-hydroxybutyric acid. The resulting raw reaction product or raw mixture can be purified by known methods, especially by removing any remaining starting compounds and/or any by-products present, and furthermore—if desired—can be separated by known methods, especially by distillation and/or chromatography (e. g. fractionation into the individual polyol esters, i. e, mono-, di-, tri- etc. polyol esters of acyl-capped (acyl-blocked) 3-hydroxybutyric acid, or else fractionation into fractions with enriched and depleted portions of individuals etc.).

In addition, the production method according to the invention, including optional further processing or purification steps, can be operated economically and can also be implemented on a large scale.

Especially, the inventive production method uses easily accessible starting compounds and furthermore allows a relatively simple process management even in case of large-scale implementation.

Nevertheless, excellent yields are achieved in accordance with the invention, wherein the formation of by-products is minimized (no significant amounts of by-products) or avoided. Furthermore, the reactants used are themselves physiologically compatible and even pharmaceutically active, so that any reactants still present can remain in the reaction product and no or hardly any purification process steps are necessary. In principle, however, it is possible and may be expedient under certain conditions, especially with regard to the organoleptic properties, to remove the reactants from the reaction product.

In contrast to conventional prior art production methods, the production method according to the invention does not use complex reactants and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i. e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

In the context of the present invention, it is preferred if the compound of general formula (I) is used in racemic form or in the form of the (R)-enantiomer. The (R)-configuration refers to the chiral carbon atom in the 3-position of the compound of the general formula (I).

According to the invention, it is preferred if, in the general formula (I), the radical $R^1$ represents ethyl.

In other words, it is preferred according to the invention if, as compound of the general formula (I), 3-acetylacetobutyric acid ethyl ester (ethyl 3-acetylacetobutyrate) of the formula $CH_3—CH(OR^2)—CH_2—C(O)OC_2H_5$, wherein the radical $R^2$ has the meaning defined hereinabove, is used. This enables particularly efficient method control and high yields with minimized or suppressed by-product formation.

Especially, in the inventive method, the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out Surprisingly, the method or reaction nevertheless proceeds with high conversion and yields and at least essentially without significant by-product formation.

According to a particular embodiment of the present invention, the reaction can be carried out in the presence of a catalyst, especially an enzyme and/or a metal-containing and/or metal-based, acidic or basic catalyst. In this particular embodiment, it is preferred if the catalyst is recycled after the reaction.

As previously stated, according to a particular embodiment of the inventive production method, the reaction may be carried out in the presence of an enzyme as a catalyst.

In this context, the enzyme can especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Within the scope of the present invention, the enzyme used as catalyst can especially be derived from *Candida antarctica, Mucor miehei* (*Rhizomucor miehei*), *Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially from *Candida antarctica, Mucor miehei* (*Rhizomucor miehei*) and *Thermomyces lanuginosus.*

According to a specific embodiment, the enzyme can be used in immobilized form, immobilized on a carrier, preferentially on a polymeric carrier, preferably on a polymeric organic carrier, more preferably with hydrophobic properties, even more preferably on a poly(meth)acrylic resin-based carrier.

As explained hereinabove with respect to the use of a catalyst in general, when an enzyme is used as a catalyst, it is preferred to recycle the enzyme after the reaction.

If the reaction is carried out in the presence of an enzyme as a catalyst within the framework of the inventive production method, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, the amount of the enzyme used can vary within wide range. Especially, the enzyme can be used in amounts, based on the total amount of the starting compounds (I) and (II), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight Nevertheless, it may be necessary to deviate from the above-mentioned amounts in individual cases or for specific applications without leaving the scope of the present invention.

If, according to a particular embodiment of the present invention, the reaction is carried out in the presence of an enzyme as a catalyst, the applied pressure range may also vary within a wide range. Especially, if the reaction is carried out in the presence of an enzyme as a catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the reaction can be carried out in the presence of a metal-containing and/or metal-based, acidic or basic catalyst.

According to this alternative embodiment of the present invention, according to which the reaction is carried out in the presence of a metal-containing and/or metal-based, acidic or basic catalyst, the catalyst can especially be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

According to this embodiment, especially an alkali or alkaline earth alcoholate can be used as a catalyst.

Especially, also according to this embodiment it is preferred if the catalyst based on the metal-containing and/or metal-based, acidic or basic catalyst is recycled after the reaction.

If, according to the particular embodiment of the present invention the reaction is carried out in the presence of a metal-containing and/or metal-based, acidic or basic catalyst, the temperatures can be varied within a wide range. Especially, the reaction can be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also according to this embodiment, the catalyst (i. e. the metal-containing and/or metal-based, acidic or basic catalyst) can also be varied within a wide quantity range: For example, the catalyst based on a metal-containing and/or metal-based, acidic or basic catalyst can be used in amounts, based on the total amount of the starting compounds (I) and (II), in the range of from 0.01 to 30% by weight, especially in the range of from 0.05 to 15% by weight, preferentially in the range of from 0.1 to 15% by weight, preferably in the range of from 0.2 to 10% by weight Nevertheless, it is possible to deviate from the above-mentioned amounts for specific applications or individual cases without leaving the scope of the present invention.

If, according to this particular embodiment of the present invention, the reaction is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds is concerned, this can also be varied within a wide range.

Taking into account process economy and optimization of the course of the method, especially with regard to the minimization of by-products, it is advantageous if the compound of the general formula (I), based on the hydroxyl groups of the polyol (II), especially polyglycerol, is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if the compound of the general formula (I) and the polyol (II), especially the polyglycerol are used in a molar ratio of compound of the general formula (I)/polyol (II) in a range of from 1:1 to 10:1, especially in a range of from 2:1 to 8:1, preferably in a range of from 3:1 to 6:1.

With regard to the compound of the general formula (I) which can be used in the method according to the invention, it is particularly preferred if the compound of the general formula (I), used as starting compound, is an acyl-capped (acyl-blocked) 3-hydroxybutyric acid or its salt or ester.

According to a particular embodiment of the present invention, it may especially be provided that the compound of the general formula (I), used as starting compound, especially the acyl-capped (acyl-blocked) 3-hydroxybutyric acid, is obtained and/or obtainable by the reaction of a compound of the general formula (IV)

$$CH_3—CH(OH)—CH_2—C(O)OR^1 \quad (IV)$$

wherein, in the general formula (IV), the radical $R^1$ represents hydrogen or $C_1$-$C_4$-alkyl, especially $C_1$-$C_4$-alkyl, preferentially methyl or ethyl, preferably ethyl, with at least one compound of the general formula (V)

$$CH_3—C(O)—CH_2—C(O)OR^3 \quad (V)$$

wherein, in the general formula (V), the radical $R^3$ represents $C_1$-$C_4$ alkyl, especially methyl or ethyl, preferably ethyl.

Especially, the reaction of the compound of general formula (IV) as defined above with the compound of general formula (V) as defined above can be carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, the reaction of the compound of the general formula (IV) as defined above with the compound of the general formula (V) as defined above can be carried out in the presence of a catalyst, especially an enzyme and/or a metal-containing and/or metal-based acidic or basic catalyst, preferentially in the presence of an enzyme. This has the advantage that especially the formation of by-products is suppressed or reduced and, furthermore, the conversion rate is increased. According to this embodiment, it is preferred if the catalyst is recycled after the reaction.

Taking into account process economy and optimization of the course of the method, especially with regard to minimization of by-products, it is advantageous if the compound of general formula (V) and the compound of the general formula (IV) are used in a molar ratio of compound of the general formula (V)/compound of the general formula (TV) in a range of from 1.1:1 to 10:1, preferably in a range of from 1.5:1 to 9:1, especially in a range of from 2:1 to 8:1, preferentially in a range of from 3:1 to 6:1. In this way, by-product formation, especially the formation of dimeric 3-hydroxybutyric acid and its acyl-capped derivatives, is efficiently counteracted.

With regard to the polyol (II) which can be used in the method according to the invention, it may especially be intended that the polyol (II) corresponds to the general formula (IIa)

$$(HO)_m—(X)—(OH)_n \quad (IIa)$$

wherein, in the general formula (IIa),

X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_{21}$-alkyl radical, or a $C_3$-$C_{21}$-(poly) alkyl ether radical, preferentially a $C_4$-$C_{21}$-(poly)alkyl ether radical, especially a $C_3$-$C_{21}$-(poly)alkylene glycol radical, preferentially a $C_4$-$C_{21}$-(poly)alkylene glycol radical, the variables m and n, each independently of one another, represent an integer from 1 to 10.

Especially, it is preferred in this context according to the invention if the hydroxyl groups of the polyol (II) are located in any position of the radical X, preferentially wherein at least one hydroxyl group is terminal (i. e. is a primary hydroxyl group). Especially, this means that the hydroxyl groups may be located or provided in any position of the organic radical X (preferentially, however, with 5 the proviso that at least one hydroxyl group is terminal and/or is a primary hydroxyl group).

According to a particular embodiment of the method according to the invention, the polyol (II) may be a polyglycerol of the general formula (IIb)

$$HO—CH_2—CH(OH)—CH_2—[O—CH_2—CH(OH)—CH]_p—OH \quad (IIb)$$

wherein, in the general formula (IIb), the variable p represents an integer from 0 to 6, especially from 1 to 4, preferentially 1 or 2, more preferably 1.

According to a further particular embodiment of the method according to the invention, the polyol (II) may be a diglycerol of formula (IIc)

$$HO—CH_2—CH(OH)—CH_2—O—CH_2—CH(OH)—CH_2—OH \quad (IIc)$$

According to a preferred embodiment of the inventive method, the polyol (II) is not propane-1,2,3-triol; i. e. the polyol (II) is not glycerol.

According to an alternative preferred embodiment of the inventive method, the polyol (II) is propane-1,2,3-triol; i. e. the polyol (II) is glycerol.

According to a further particular embodiment of the method according to the invention, the polyol (II) may be selected from alkanediols, especially $C_3$-$C_{21}$-alkanediols, preferentially $C_4$-$C_{21}$-alkanediols, preferably linear or branched alkanediols, more preferably linear or branched $C_3$-$C_{21}$-alkanediols, preferentially $C_4$-$C_{21}$-alkanediols, even more preferably linear $C_3$-$C_{21}$-alkanediols, preferentially $C_4$-$C_{21}$-alkanediols, further preferably linear $C_3$-$C_{21}$-alkanediols, preferentially $C_4$-$C_2$-alkanediols, having at least one terminal and/or primary hydroxyl group, yet even more preferably pentanediol, especially 1,2-pentanediol.

According to a preferred embodiment of the present invention, the present invention according to this aspect of the invention relates to a method for producing polyol esters, especially polyglycerol esters, of acyl-capped (acyl-blocked) 3-hydroxybutyric acid (beta-hydroxybutyric acid, 3-hydroxybutanoic acid), especially as defined hereinabove, wherein at least one compound of the general formula (I)

$$CH_3—CH(OR^2)—CH_2—C(O)OR^1 \quad (I)$$

wherein, in the general formula (I), the radical $R^1$ represents ethyl and the radical $R^2$ represents a radical $CH_3—C(O)—CH_2—C(O)—$, is reacted with at least one polyol (II) comprising at least two, especially at least three, hydroxyl groups (OH-groups), especially polyglycerol, wherein the polyol (II) is selected from polyglycerols of the general formula (IIb)

$$HO—CH_2—CH(OH)—CH_2—[O—CH_2—CH(OH)—CH]_p—OH \quad (IIb)$$

wherein, in the general formula (IIb), the variable p represents an integer from 0 to 6, especially from 1 to 4, preferentially 1 or 2, more preferably 1, so that, as a reaction product, one or more acyl-capped (acyl-blocked) 3-hydroxybutyric acid polyol esters (III), especially 3-hydroxybutyric acid polyglycerol esters, are obtained.

A particularly preferred approach according to the invention is illustrated by the following reaction or synthesis scheme (with "EtOH"=ethanol) (wherein, depending on the reaction control, either individual esters or a mixture of two or more thereof are obtained):

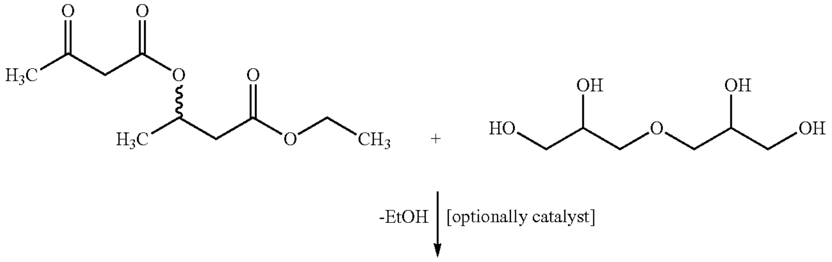

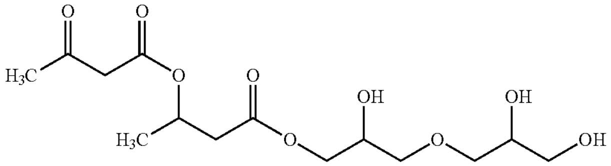

monoester

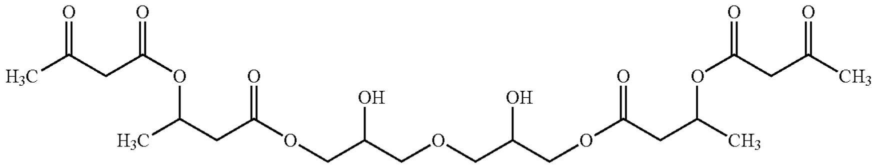

diester

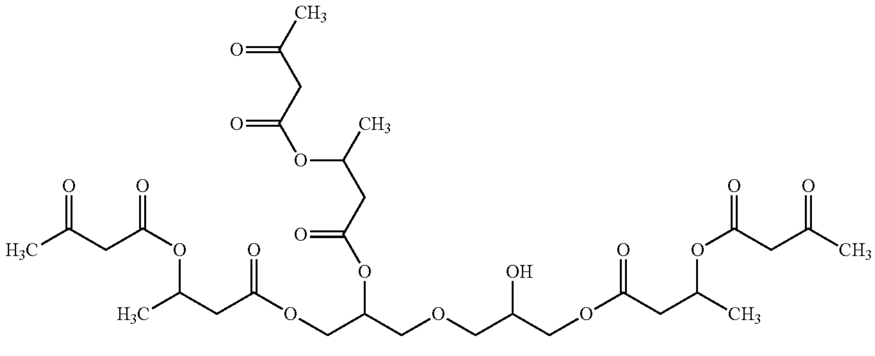

triester

-continued

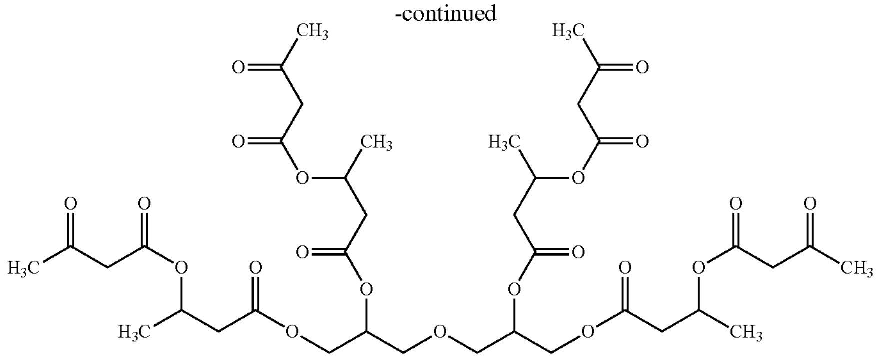

tetraester

In the method according to the invention, during the reaction, the compound according to the general formula (VI)

$$R^1\text{—OH} \quad (VI)$$

is formed simultaneously, wherein, in the general formula (VI), the radical $R^1$ represents hydrogen or $C_1$-$C_4$-alkyl, especially $C_1$-$C_4$-alkyl, preferentially methyl or ethyl, preferably ethyl.

Especially it is preferred in this context if the compound according to general formula (VI) is withdrawn from the reaction, especially continuously withdrawn, especially by means of preferentially continuous removal by distillation. In this way, the reaction equilibrium is efficiently shifted to the side of the reaction products. Also, the formation of by-products is minimized or prevented in this way.

Within the framework of the production method according to the invention, the reaction product, especially the composition of the reaction product, especially the presence of various and/or different acyl-capped 3-hydroxybutyric acid polyol esters (III), especially 3-hydroxybutyric acid polyglycerol esters, and their proportion in the case of a mixture, may be controlled and/or regulated by means of the reaction conditions, especially by selecting the reaction temperature (conversion temperature) and/or by selecting the reaction pressure (conversion pressure) and/or by providing a catalyst and selecting such catalyst with respect to the type and/or amount and/or by selecting the amounts of starting compounds (reactants) and/or by providing the removal of the compound according to the general formula (VI) as defined hereinabove.

Following the reaction, the reaction product obtained can be subjected to further conventional or per se known purification or work-up steps.

In this context, the reaction product obtained can be fractionated after the reaction has taken place, especially fractionated by distillation.

Also, unreacted starting compounds (I) and/or (II) can be separated from the reaction product and subsequently recycled. This enables a particularly economical method control.

According to a particularly preferred embodiment of the present invention, the present invention according to this aspect of the invention relates to a method for producing polyol esters, especially polyglycerol esters, of acyl-capped (acyl-blocked) 3-hydroxybutyric acid, especially a method as defined hereinabove, (a) wherein, in a first process step (a), at least one compound of the general formula (IV)

$$CH_3\text{—}CH(O)\text{—}CH_2\text{—}C(O)OR^1 \quad (IV)$$

wherein, in the general formula (IV), the radical $R^1$ represents hydrogen or $C_1$-$C_4$-alkyl, especially $C_1$-$C_4$-alkyl, preferentially methyl or ethyl, preferably ethyl, is reacted with at least one compound of the general formula (V)

$$CH_3\text{—}C(O)\text{—}CH_2\text{—}C(O)OR^3 \quad (V)$$

wherein, in the general formula (V), the radical R represents $C_1$-$C_4$-alkyl, especially methyl or ethyl, preferably ethyl, so that a compound of the general formula (I)

$$CH_3\text{—}CH(OR^2)\text{—}CH_2\text{—}C(O)OR^1 \quad (I)$$

wherein, in the general formula (I), the radical $R^1$ has the meaning defined hereinabove and the radical $R^2$ represents a radical $CH_3$—C(O)—$CH_2$—C(O)— is formed; and subsequently (b) in a second process step (b), the compound of the general formula (I) obtained in this way, as defined hereinabove, is reacted with at least one polyol (II) comprising at least two, especially at least three, hydroxyl groups (OH-groups), especially polyglycerol, as defined hereinabove, so that, as a reaction product, at least one acyl-capped (acyl-blocked) 3-hydroxybutyric acid polyol ester (III), especially 3-hydroxybutyric acid polyglycerol ester, is obtained A particularly preferred procedure according to the invention, consisting of the synthesis of the acyl-capped (acyl-blocked)ethyl 3-hydroxybutyric acid ester and subsequent reaction with diglycerol, is illustrated by the following reaction or synthesis scheme (wherein, depending on the reaction control, either individual esters or a mixture of two or more thereof are obtained):

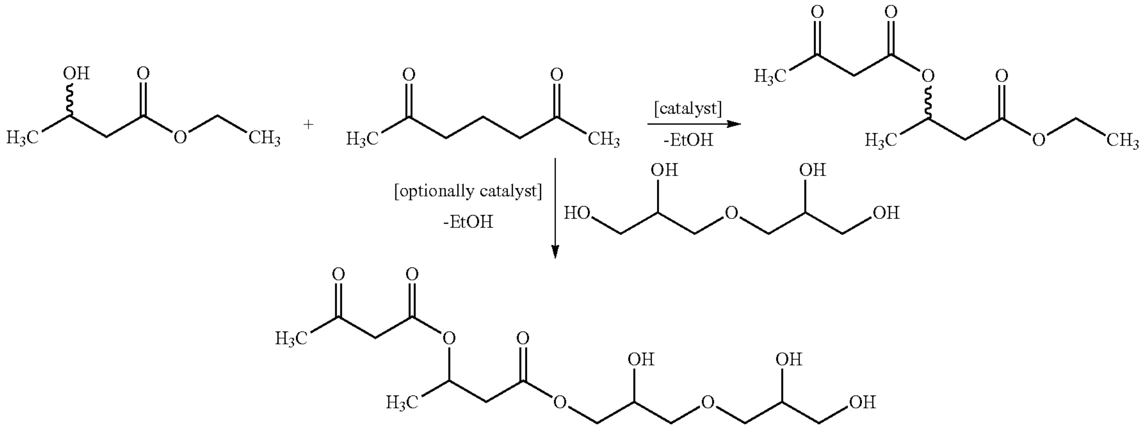

monoester

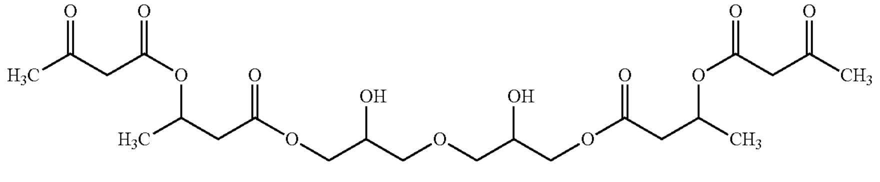

diester

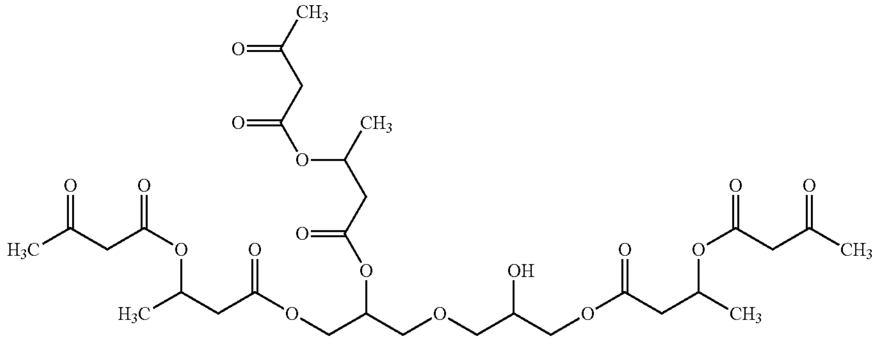

triester

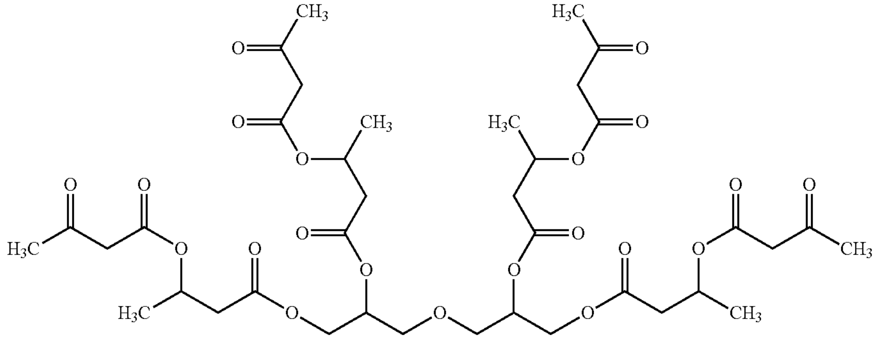

tetraester

According to a particular embodiment of the production method according to the invention, it is especially possible to proceed such that hydroxyl groups still present in the reaction product after the reaction has taken place are at least partially, preferentially completely, functionalized, especially esterified.

In other words, according to a particular embodiment according to the invention, the reaction can be followed by a partial, especially complete, functionalization, especially esterification, of hydroxyl groups still present.

In this particular embodiment of the method according to the invention, especially the functionalization, especially esterification, of the hydroxyl groups still present in the reaction product after the reaction has taken place, can be carried out with at least one carboxylic acid anhydride of the general formula (VII)

$$R^4—O—R^4 \qquad (VII)$$

wherein, in the general formula (VII), the radical $R^4$, each independently of one another, identical or different, represents a radical of the type linear (straight-chain) or branched, saturated or mono- or polyunsaturated ($C_1$-$C_{13}$-alkyl)-C(O)—, especially ($C_4$-$C_{33}$-alkyl)-C(O)—, preferentially ($C_7$-$C_{33}$-alkyl)-C(O)—.

In this particular embodiment of the method according to the invention, it is preferred if, in the general formula (VII), the radical $R^4$, each independently of one another, identical or different, is a fatty acid radical, especially a $C_5$-$C_{34}$-fatty acid radical, preferentially a $C_8$-$C_{34}$-fatty acid radical.

Furthermore, in this particular embodiment of the method according to the invention, it is preferred if the carboxylic acid anhydride of the general formula (VII) is a fatty acid anhydride, especially a $C_5$-$C_{34}$-fatty acid anhydride, preferentially a $C_8$-$C_{34}$-fatty acid anhydride.

Especially, it is preferred if, as carboxylic acid anhydride of the general formula (VII), a compound is used in which the radicals $R^4$ are identical. In other words, as carboxylic acid anhydride of the general formula (VII), a symmetrical carboxylic acid anhydride is used.

According to an alternative embodiment, it is preferred if, as carboxylic acid anhydride of the general formula (VII), a compound is used in which the radicals $R^4$ are different from one another. In other words, as carboxylic acid anhydride of the general formula (VII), an asymmetric carboxylic acid anhydride is used.

According to the invention, the functionalization of the hydroxyl groups still present in the reaction product after the reaction has taken place with the at least one carboxylic acid anhydride of the general formula (VII) may be carried out at temperatures in the range of from 60 to 150° C., especially in the range of from 70 to 120° C., preferentially in the range of from 80 to 100° C.

The inventive functionalization of the hydroxyl groups still present in the reaction product after the reaction has taken place with the at least one carboxylic acid anhydride of the general formula (VII) may especially be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

Especially, it is preferred if the functionalization of the hydroxyl groups still present in the reaction product after the reaction has taken place with the at least one carboxylic acid anhydride of the general formula (VII) is carried out in the absence of solvents and/or without any solvent. That is, the reaction is thus carried out as a reaction in mass or as a reaction in substance or as a so-called bulk reaction. This has the advantage that the reaction products obtained are not contaminated with solvent and no solvent has to be removed and disposed of or recycled in a costly and energy-intensive manner after the method or reaction has been carried out. Surprisingly, the method or reaction nevertheless proceeds with high conversions and yields and at least substantially without significant by-product formation.

In the course of the inventive functionalization of the hydroxyl groups still present in the reaction product after the reaction has taken place with the at least one carboxylic acid anhydride of the general formula (VII), a compound according to the general formula (VIII)

$$R^4\text{—}OH \qquad \text{(VIII)}$$

is formed simultaneously, wherein the radical $R^4$ has the meaning defined hereinabove.

Especially, it is preferred in this context if the compound according to the general formula (Vill) is withdrawn during or after the reaction, especially after the reaction has taken place, preferentially by distillation.

Following the inventive functionalization of the hydroxyl groups still present in the reaction product after the reaction has taken place with the at least one carboxylic acid anhydride of the general formula (VII), the product obtained can be subjected to further conventional or per se known purification or work-up steps.

In this context, the functionalization is followed by a distillation and/or a chromatography, preferentially a distillation. Especially, any reactants and reaction by-products still present, especially compounds according to the general formula (VIII), are distilled off.

In the context of the functionalization according to the invention, it is provided that, in case the radicals $R^4$ in the general formula (VII) are different from one another, and/or in case the radicals $R^4$ in the general formula (VII) each represent an alkyl radical having more than two carbon atoms, the carboxylic acid anhydride of the general formula (VII) is obtainable and/or is obtained by reacting acetic anhydride with at least one carboxylic acid, especially fatty acid, of the general formula (VIII)

$$R^4\text{—}OH \qquad \text{(VIII)}$$

wherein the radical $R^4$ has the meaning defined hereinabove.

In this context, the reaction of acetic anhydride with the at least one carboxylic acid, especially fatty acid, of the general formula (VIII) takes place according to the reaction equation $$[(CH_3\text{—}C(O)]_2O + 2\,R^4\text{—}OH \xrightarrow{-2\,CH_3COOH} R^4\text{—}O\text{—}R^4$$

wherein the radical $R^4$ has the meaning defined hereinabove, however, with the proviso that the radicals $R^4$ are different from one another, and/or that the radicals $R^4$, each independently of one another, represent an alkyl radical having more than two carbon atoms.

According to a particular embodiment of this method according to the invention, a symmetrical carboxylic acid anhydride of the general formula (VII) is produced. In other words, in the general formula (VII), the $R^4$ radicals are identical and represent an alkyl radical having more than two carbon atoms.

According to an alternative particular embodiment of this method according to the invention, an asymmetric carboxylic acid anhydride of the general formula (VII) is produced. Thus, in the general formula (VII), the $R^4$ radicals are different from one another, preferentially, in the general formula (VII), the $R^4$ radicals each represent an alkyl radical having more than two carbon atoms.

A particularly preferred procedure according to the invention, which provides a functionalization, especially esterification, of hydroxyl groups still present (completely or partially) following the reaction, is illustrated by the following reaction or synthesis scheme (wherein, depending on the reaction procedure during the reaction, either individual esters or a mixture of two or more thereof are obtained and wherein, in the following reaction or synthesis scheme, the radical R denotes hydrogen or a radical of the formula $CH_3\text{—}(CH_2)_{x=0\text{-}28}\text{—}C(O)\text{—}$):

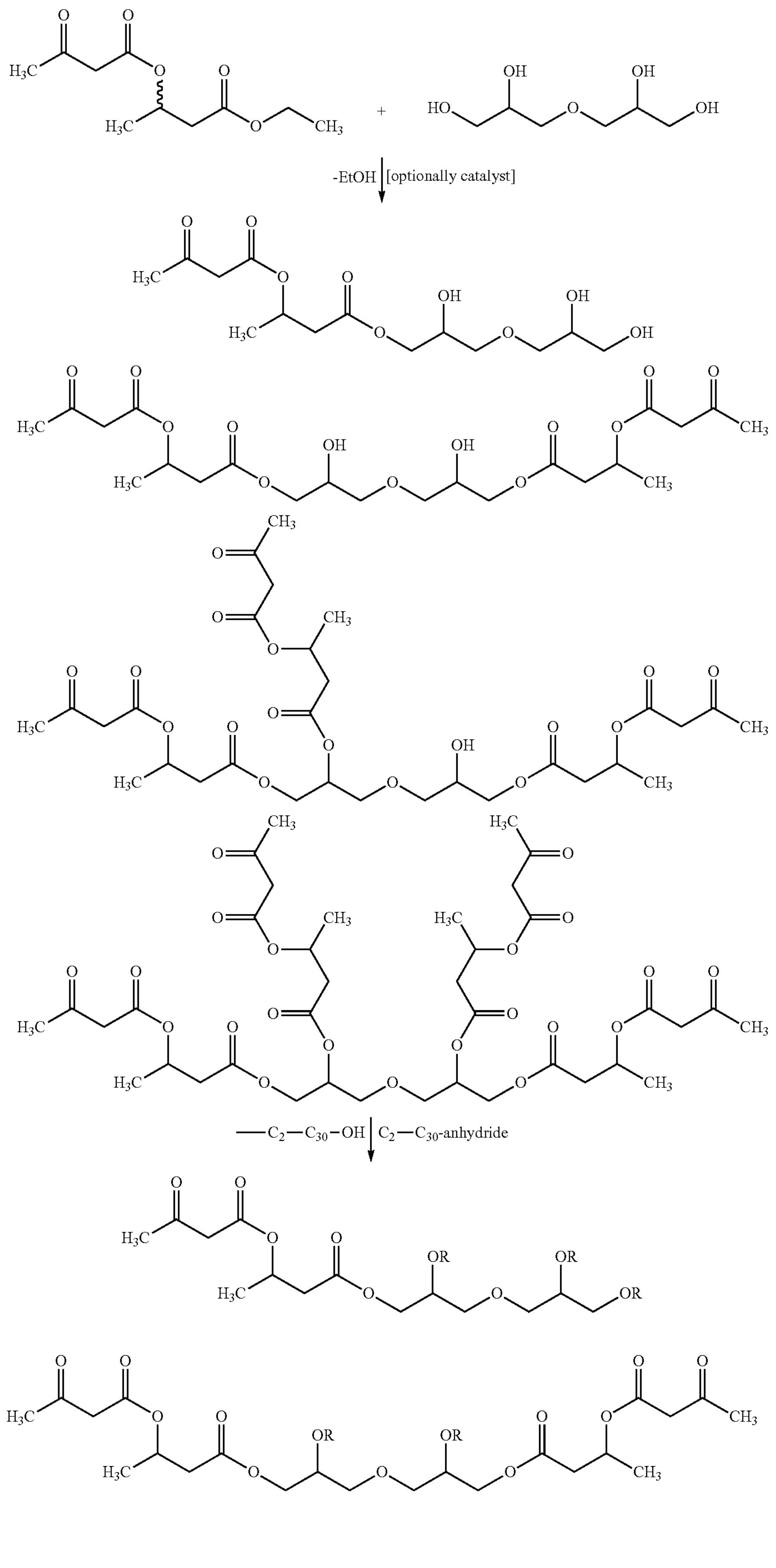
-EtOH
[optionally catalyst]
—C2—C30-OH
C2—C30-anhydride

-continued

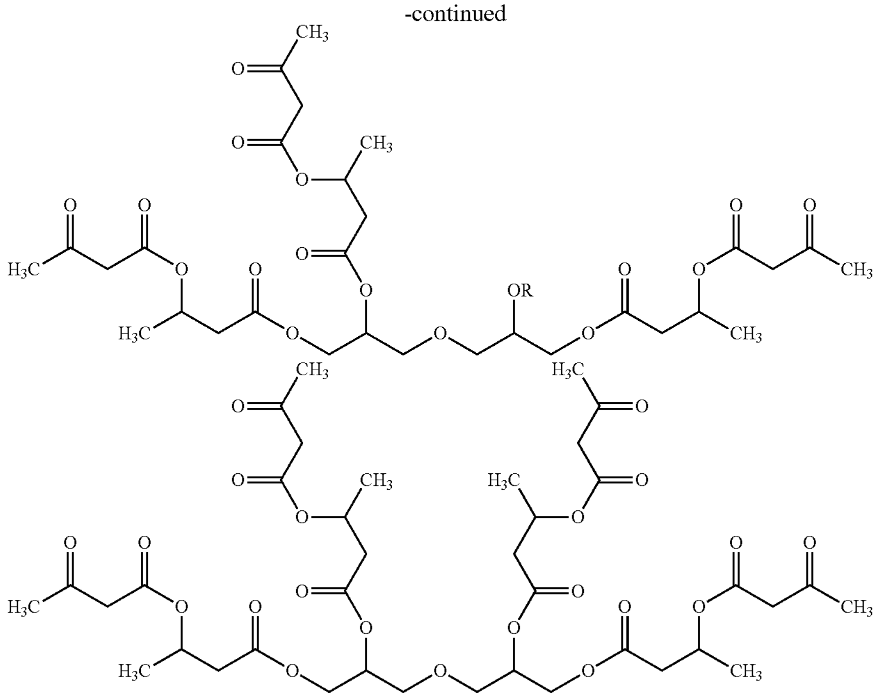

According to an alternative embodiment of the functionalization, especially esterification, of the hydroxyl groups still present in the reaction product after the reaction has taken place, the functionalization can be carried out by reaction with at least one carboxylic acid and/or a carboxylic acid ester of the general formula (IX)

$$R^4—O—R^8 \quad (IX)$$

wherein, in the general formula (IX), a the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$alkyl)-C (O)—, the radical $R^8$ represents hydrogen or $C_1$-$C_4$-alkyl, especially methyl or ethyl, preferably hydrogen.

In this context, it is particularly preferred if the carboxylic acid and/or the carboxylic acid ester of the general formula (IX) represents a fatty acid and/or a fatty acid ester, especially a $C_5$-$C_{34}$-fatty acid and/or a $C_5$-$C_{34}$-fatty acid ester, preferentially a $C_8$-$C_{34}$-fatty acid and/or a $C_8$-$C_{34}$-fatty acid ester.

Especially, this embodiment according to the invention of the functionalization of the hydroxyl groups still present in the reaction product after the reaction has taken place with at least one carboxylic acid and/or a carboxylic acid ester of the general formula (IX) is carried out in the absence of solvents and/or without any solvent That is, the reaction is thus carried out as a reaction in mass and/or as a reaction in substance and/or as a so-called bulk reaction. This has the advantage that the reaction products obtained are not contaminated with solvent and no solvent has to be removed and disposed of or recycled in a costly and energy-intensive manner after the method or reaction has been carried out Surprisingly, the method or reaction nevertheless proceeds with high conversions and yields and at least substantially without significant by-product formation.

According to a preferred embodiment, the functionalization of the hydroxyl groups still present in the reaction product after the reaction has taken place with at least one carboxylic acid and/or a carboxylic acid ester of the general formula (IX) is carried out in the presence of a catalyst, especially an enzyme and/or a metal-containing and/or metal-based, acidic or basic catalyst.

In this context, it is particularly preferred if the catalyst is recycled after the reaction.

As previously stated, according to a preferred embodiment, the functionalization of the hydroxyl groups still present in the reaction product after reaction has taken place with at least one carboxylic acid and/or a carboxylic acid ester of the general formula (IX) may be carried out in the presence of an enzyme as a catalyst.

Especially, the enzyme may be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

In this particular embodiment, the enzyme used as a catalyst may be derived from *Candida antarctica, Mucor miehei* (*Rhizomucor miehei*), *Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially of *Candida antarctica, Mucor miehei* (*Rhizomucor miehei*) and *Thermomyces lanuginosus.*

In this context, it is particularly preferred if the enzyme is used in immobilized form, especially immobilized on a carrier, preferentially on a polymeric carrier, preferably on a polymeric organic carrier, more preferably with hydrophobic properties, even more preferably on a poly(meth)acrylic resin-based carrier.

As already stated in connection with the catalyst in general, it is preferred if the enzyme is recycled after the reaction.

Insofar as the inventive functionalization of the hydroxyl groups still present in the reaction product after the reaction has taken place is carried with at least one carboxylic acid and/or a carboxylic acid ester of the general formula (IX) in the presence of an enzyme as a catalyst, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, the amount of the enzyme used may vary within a wide range. Especially, the enzyme can be used in amounts, based on the total amount of starting compounds, in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight Nevertheless, it may be necessary to deviate from the aforementioned amounts on an individual or application-related basis without leaving the scope of the present invention. In this context, the starting compounds are the acyl-capped (acyl-blocked) 3-hydroxybutyric acid polyol ester (III) and the carboxylic acid and/or the carboxylic acid ester of the general formula (IX).

If, according to a particular embodiment of the present invention, the functionalization of the hydroxyl groups still present in the reaction product after the reaction has taken place is carried out with at least one carboxylic acid and/or a carboxylic acid ester of the general formula (IX) in the presence of an enzyme as a catalyst, the pressure range used may also vary within a wide range. Especially, when the reaction is carried out in the presence of an enzyme as a catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the inventive functionalization of the hydroxyl groups still present in the reaction product after the reaction has taken place with at least one carboxylic acid and/or a carboxylic acid ester of the general formula (IX), the functionalization may be carried out in the presence of a metal-containing and/or metal-based, acidic or basic catalyst.

According to this alternative embodiment of the functionalization according to the invention, according to which the functionalization is carried out in the presence of a metal-containing and/or metal-based, acidic or basic catalyst, the catalyst may especially be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

In this embodiment, the catalyst may especially be an alkali or an alkaline earth metal alcoholate.

Especially, it is also preferred in this embodiment of the functionalization if the catalyst based on the metal-containing and/or metal-based acidic or basic catalyst is recycled after the reaction.

If, according to this particular embodiment of the present invention, the functionalization of the hydroxyl groups still present in the reaction product after the reaction has taken place with at least one carboxylic acid and/or a carboxylic acid ester of the general formula (IX) is carried out in the presence of a metal-containing and/or metal-based acidic or basic catalyst, the temperatures can be varied within a wide range. Especially, the reaction can be carried out in the presence of a metal-containing and/or metal-based acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also in this embodiment, the catalyst (i. e. the metal-containing and/or metal-based, acidic or basic catalyst) can be varied within a wide quantity range: Thus, the catalyst based on a metal-containing and/or metal-based, acidic or basic catalyst can be used in amounts, based on the total amount of starting compounds, in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight, Nevertheless, it is possible, depending on the application or individual case, to deviate from the above-mentioned amounts without leaving the scope of the present invention. In this context, the starting compounds are the acyl-capped (acyl-blocked) 3-hydroxybutyric acid polyol ester (III) and the carboxylic acid and/or the carboxylic acid ester of the general formula (IX).

When, according to this particular embodiment of the present invention, the functionalization of the hydroxyl groups still present in the reaction product after the reaction has taken place with at least one carboxylic acid and/or a carboxylic acid ester of general formula (IX) is carried out in the presence of a metal-containing and/or metal-based acidic or basic catalyst, the pressure range may equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

In this particular embodiment of the functionalization of the hydroxyl groups still present in the reaction product after the reaction with at least one carboxylic acid and/or a carboxylic acid ester of the general formula (IX), a compound of the general formula (XI)

$$R^8\text{—OH} \qquad \text{(XI)}$$

is formed simultaneously, wherein the radical RE has the meaning defined hereinabove.

Especially, it is preferred in this context if the compound of the general formula (XI) is withdrawn during or after the reaction has taken place, especially during the reaction, preferentially by distillation. In this way, the reaction equilibrium is efficiently shifted to the side of the reaction products. Also, in this way, the formation of by-products is minimized or prevented.

According to a particular embodiment of the method according to the invention, the ester groups introduced in the reaction product (III) by the method described hereinabove can be subjected to partial transesterification by means of a compound of general formula (IX) as defined hereinabove.

In other words, the ester groups introduced in the reaction product (III) by the method described hereinbefore can be partially exchanged by means of transesterification by a radical $R^4$ having the meaning defined hereinabove.

In this context, the transesterification according to this particular embodiment of the present invention may be carried out under reaction conditions as described hereinabove regarding the functionalization according to the invention of the hydroxyl groups still present in the reaction product after the reaction has taken place with at least one carboxylic acid and/or a carboxylic acid ester.

Furthermore, the present invention relates—according to a second aspect of the present invention—to a method for producing functionalized, especially fatty acid functionalized, preferentially $C_5$-$C_{34}$-fatty acid functionalized, preferably $C_8$-$C_{34}$-fatty acid functionalized, polyol esters, especially polyglycerol esters, of acyl-capped (acyl-blocked) 3-hydroxybutyric acid (beta-hydroxybutyric acid, 3-hydroxybutanoic acid), (A) wherein, according to a (first) synthesis route (A), first in a first process step at least one compound of the general formula (I)

$$CH_3—CH(OR_2)—CH_2—C(O)OR^1 \quad (I)$$

wherein, in the general formula (I), the radical $R^1$ represents hydrogen or $C_1$-$C_4$-alkyl, especially $C_1$-$C_4$-alkyl, preferentially methyl or ethyl, preferably ethyl, and the radical $R^2$ represents a radical $CH_3—C(O)—CH_2—C(O)—$, is reacted with at least one polyol (II) comprising at least two, especially at least three, hydroxyl groups (OH-groups), especially polyglycerol, especially as defined in any of the preceding claims, followed by a second process step, wherein the second process step comprises (i) an at least partial functionalization, especially an at least partial esterification, of hydroxyl groups still present by means of at least one fatty acid and/or its ester or anhydride, especially by means of at least one $C_5$-$C_{34}$-fatty acid and/or its ester or anhydride, preferentially by means of at least one $C_8$-$C_{34}$-fatty acid and/or its ester or anhydride, and/or (ii) a partial transesterification of ester groups introduced in the first process step by means of at least one fatty acid and/or its ester, especially by means of at least one $C_5$-$C_{34}$-fatty acid and/or its ester, preferentially by means of at least one $C_8$-$C_{33}$-fatty acid and/or its ester;

or else (B) wherein according to a (second, alternative to (A)) synthesis route (B) first in a first process step at least one polyol (II) comprising at least two, especially at least three, hydroxyl groups (OH-groups), especially polyglycerol, especially as defined in any of the preceding claims, is reacted with at least one fatty acid and/or its ester or anhydride, especially with at least one $C_5$-$C_{34}$-fatty acid and/or its ester or anhydride, preferentially with at least one $C_8$-$C_{34}$-fatty acid and/or its ester or anhydride, followed by a second process step, wherein the second process step comprises (i) an at least partial esterification of hydroxyl groups still present by means of a compound of the general formula (I) as defined hereinabove, and/or (ii) a partial transesterification of ester groups introduced in the first process step by means of a compound of the general formula (I) as defined hereinabove;

so that, as reaction product, in each case one or more functionalized, especially fatty acid functionalized, preferentially $C_5$-$C_{33}$-fatty acid functionalized, preferably $C_8$-$C_{34}$-fatty acid functionalized, acyl-capped (acyl-blocked) 3-hydroxybutyric acid polyol esters (III'), preferably one or more functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyglycerol esters, are obtained.

Especially, the production method according to the invention, according to synthesis route (A), can be carried out according to the inventive method described hereinabove.

With regard to the fatty acid and/or fatty acid ester which can be used in the method according to the invention according to synthesis route (B), it is particularly preferred if the fatty acid and/or the fatty acid ester is a carboxylic acid and/or a carboxylic acid ester of the general formula (IX) as defined hereinabove.

Furthermore, with regard to the fatty acid anhydride which can be used in the method according to the invention, according to synthesis route (B), it is particularly preferred if the fatty acid anhydride is a carboxylic acid anhydride of the general formula (VII) as defined hereinabove.

Especially, in the inventive method, according to synthesis route (B), in the first process step the reaction is carried out in the absence of solvents and/or without any solvent. As previously stated, this means that the reaction is thus carried out as a reaction in mass or as a reaction in substance or as a so-called bulk reaction. This has the advantage that the reaction products obtained are not contaminated with solvent and no solvent has to be removed and disposed of or recycled in a costly and energy-consuming manner after the method or reaction has been carried out Surprisingly, the method or reaction nevertheless proceeds with high conversions and yields and at least substantially without significant by-product formation.

According to a particular embodiment of the method of the invention, according to synthesis route (B), in the first process step, in case of using fatty acid and/or its ester as a starting material, the reaction may be carried out in the presence of a catalyst, especially a metal-containing and/or metal-based, acidic or basic catalyst.

In this context, it is particularly preferred if the catalyst is recycled after the reaction.

Alternatively to this particular embodiment, according to synthesis route (B), in case of using fatty acid anhydride as a starting material, the reaction is carried out in the absence of a catalyst and/or without any catalyst.

As previously stated, according to a particular embodiment of the inventive production method, according to synthesis route (B), in the first process step, in case of using fatty acid and/or its ester as a starting material, the reaction may be carried out in the presence of a metal-containing and/or metal-based, acidic or basic catalyst.

The catalyst may be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

In this embodiment, the catalyst may especially be an alkali or an alkaline earth metal alcoholate.

Especially, in this context, as previously mentioned, it is preferred if the catalyst is recycled after the reaction.

If, according to the particular embodiment, the reaction is carried out in the presence of a metal-containing and/or metal-based, acidic or basic catalyst, it is preferred if the reaction is carried out at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Especially, according to this embodiment, it is also preferred if the catalyst is used in amounts, based on the total amount of starting compounds, in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight.

Furthermore, according to this embodiment, it is preferred if the reaction is carried out in the presence of a metal-containing and/or metal-based acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

Within the scope of the inventive production method, according to synthesis route (B), in case of using fatty acid and/or its ester as a starting material in the reaction, the compound of the general formula (XI) as defined hereinabove is formed simultaneously.

In this context, it is particularly preferred if the compound of the general formula (XI) is withdrawn during or after the reaction has taken place, especially during the reaction, preferentially by distillation.

In the inventive production method, according to synthesis route (B), in case of using fatty acid anhydride as a starting material in the reaction, the compound of the general formula (VIII) as defined hereinabove is formed simultaneously.

Especially, it is preferred if the compound of general formula (VIII) is withdrawn during or after the reaction has taken place, preferentially by distillation.

Especially, in the method according to the invention, according to synthesis route (B), the second process step is also carried out in the absence of solvents and/or without any solvent.

Furthermore, in the method according to the invention, according to synthesis route (B), the second process step is also carried out in the presence of a catalyst, especially a metal-containing and/or metal-based, acidic or basic catalyst, especially as defined hereinabove.

Also in this context, it is preferred if the catalyst is recycled after the reaction.

In this particular embodiment of the inventive method, according to synthesis route (B), in the second process step the compound of the general formula (X)

$$R^1—O—R^5 \qquad (X)$$

is formed simultaneously, wherein, in the general formula (X),

- the radical $R^1$ represents hydrogen or $C_1$-$C_4$-alkyl, especially $C_1$-$C_4$-alkyl, preferentially methyl or ethyl, preferably ethyl,
- the radical $R^5$, each independently of one another, identical or different, represents hydrogen or a radical $R^4$ as defined hereinabove.

In this context, it is particularly intended that the compound of general formula (X) is withdrawn during or after the reaction has taken place, preferentially by distillation.

According to the invention, it is particularly intended that the fatty acid, preferentially the $C_5$-$C_{34}$-fatty acid, preferably the $C_8$-$C_{34}$-fatty acid, especially in free form or in the form of its ester or anhydride, is selected from the group of caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, lignoceric acid, cerotinic acid, montanic acid, melissic acid, lacceric acid, geddic acid, undecylic acid, myristoleic acid, palmitoleic acid, margaroleic acid, petroselic acid, oleic acid, elaidic acid, vaccenic acid, gadoleic acid, cetoleic acid, erucic acid, nervonic acid, linoleic acid, linolenic acids, calendulic acid, punicic acid, eleostearic acids, stearidonic acid, arachidonic acid, eicosapentaenoic acid, docosadienoic acid, docosatetraenoic acid, docosapentaenoic acid, docosahexaenoic acid and tetracosahexaenoic acid, as well as mixtures thereof.

According to a particular embodiment of the present invention, it is preferred if the fatty acid, preferentially the $C_5$-$C_{34}$ fatty acid, preferably the $C_3$-$C_{34}$ fatty acid, especially in free form or in the form of its ester or anhydride, is selected from the group of myristic acid, pentadecanoic acid, palmitoleic acid, cetoleic acid, oleic acid, gadoleic acid cetoleic acid, erucic acid, arachidonic acid, eicosapentaenoic acid, docosadienoic acid, docosatetraenoic acid, docosapentaenoic acid, docosahexaenoic acid, tetracosahexaenoic acid as well as mixtures thereof, preferentially eicosapentaenoic acid and docosahexaenoic acid as well as mixtures thereof.

According to a further particular embodiment, the fatty acid, preferentially the $C_5$-$C_{34}$ fatty acid, preferably the $C_8$-$C_{34}$ fatty acid, especially in free form or in the form of its ester or anhydride, is selected from the group of fatty acids based on fish oil and/or occurring in fish oils, especially eicosapentaenoic acid, docosahexaenoic acid, docosatetraenoic acid, docosapentaenoic acid, docosahexaenoic acid and tetracosahexaenoic acid as well as mixtures thereof, preferentially eicosapentaenoic acid, docosahexaenoic acid as well as mixtures thereof.

In the method according to the invention, as a reaction product, one or more optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyol esters (III"), especially 3-hydroxybutyric acid polyglycerol esters, may be obtained.

Furthermore, in the inventive method, as a reaction product, one or more acyl-capped (acyl-blocked) 3-hydroxybutyric acid polyol esters (III), especially 3-hydroxybutyric acid polyglycerol esters, may be obtained.

Moreover, in the inventive method, as a reaction product, one or more functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyol esters (III'), especially 3-hydroxybutyric acid polyglycerol esters, may be obtained.

A further subject-matter—according to a third aspect of the present invention—is a reaction product or polyol ester, especially polyglycerol ester, of acyl-capped (acyl-blocked) 3-hydroxybutyric acid (beta-hydroxybutyric acid, 3-hydroxybutanoic acid), or mixtures thereof, obtainable by the method or methods of the invention.

Especially, the reaction product, especially the (chemical) product or product mixture obtainable by the method or methods of the invention may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyol esters (III"), especially 3-hydroxybutyric acid polyglycerol esters, of the general formula (III")

$$(R^6O)_m—(X)—(OR^6)_n \quad \text{(IIIa")}$$

wherein, in the general formula (IIIa"),

- X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_{21}$-alkyl radical, or a $C_3$-$C_{21}$-(poly)alkyl ether radical, preferentially a $C_4$-$C_{21}$-(poly)alkyl ether radical, especially a $C_3$-$C_{21}$-(poly)alkylene glycol radical, preferentially a $C_4$-$C_{21}$-(poly)alkylene glycol radical,
- the variables m and n, each independently of one another, represent an integer from 1 to 10,
- the radical $R^6$, each independently of one another, identical or different, represents: hydrogen or a radical $R^2$, wherein the radical $R^2$ represents a radical CH—C(O) $CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals RE, represents a radical R as defined hereinabove;

especially wherein the groups $R^6O$—are in any position of the radical X, preferentially wherein at least one group $R^6O$—is terminal.

According to a particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyglycerol esters of the general formula (IIIb")

$$R^6O—CH_2—CH(OR^6)—CH_2—[O—CH_2—CH(OR^6)—CH_2]_p—OR^6 \quad \text{(IIb")}$$

wherein, in the general formula (IIIb"),

- the variable p represents an integer from 0 to 6, especially from 1 to 4, preferentially 1 or 2, more preferably 1,
- the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C^7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents a radical $R^2$ as defined hereinabove.

According to another particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyglycerol esters of the general formula (III")

$$R^6O—CH_2—CH(OR^6)—CH_2—O—CH_2—CH(OR^6)—CH_2—OR^6 \quad \text{(IIIc")}$$

wherein, in the general formula (IIIc"), the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents a radical $R^2$ as defined hereinabove.

According to an alternative particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyglycerol esters of the general formula (IIId")

$$R^6O—CH_2—CH(OR^6)—CH_2—OR^6 \quad \text{(IIId")}$$

wherein, in the general formula (IIId"), the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents a radical $R^2$ as defined hereinabove.

According to a particular embodiment of the present invention, the reaction product may especially comprise a mixture of at least two different optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyol esters (III"), especially 3-hydroxybutyric acid polyglycerol esters, especially as defined hereinabove.

According to a further particular embodiment of the present invention, the reaction product may especially comprise a mixture of at least three different optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyol esters (III"), especially 3-hydroxybutyric acid polyglycerol esters, especially as defined hereinabove.

Especially, the reaction product (i. e. the (chemical) product or product mixture) obtainable according to the inventive method or the inventive reaction product may comprise one or more acyl-capped (acyl-blocked) 3-hydroxybutyric acid polyol esters (III), especially 3-hydroxybutyric acid polyglycerol esters, of the general formula (IIIa)

$$(R^7O)_m—(X)—(OR^7)_n \quad \text{(IIIa)}$$

wherein, in the general formula (IIIa),

X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_{21}$-alkyl radical, or a $C_3$-$C_{21}$-(poly)alkyl ether radical, preferentially a $C_4$-$C_{21}$-(poly)alkyl ether radical, especially a $C_3$-$C_{21}$-(poly)alkylene glycol radical, preferentially a $C_4$-$C_{21}$-(poly)alkylene glycol radical, the variables m and n, each independently of one another, represent an integer from 1 to 10, the radical $R^7$, each independently of one another, identical or different, represents: hydrogen or a radical $R^2$, wherein the radical $R^2$ represents a radical $CH_3—C(O)—CH_2—C(O)—$, however, with the proviso that at least one radical $R^7$, especially at least two radicals $R^7$, does not represent hydrogen;

especially wherein the groups $R^7O—$ are in any position of the radical X, preferentially wherein at least one group $R^7O—$ is terminal.

Especially, the reaction product may comprise one or more acyl-capped (acyl-blocked) 3-hydroxybutyric acid polyglycerol esters of the general formula (IIIb)

$$R^7O—CH_2—CH(OR^7)—CH_2—[O—CH_2—CH(OR^7)—CH_2]_p—OR^7 \quad \text{(IIIb)}$$

wherein, in the general formula (IIIb), the variable p represents an integer from 0 to 6, especially from 1 to 4, preferentially 1 or 2, more preferably 1, the radical $R^7$, each independently of one another, identical or different, represents: hydrogen or a radical $R^2$, wherein the radical $R^2$ represents a radical $CH_3—C(O)—CH_2—C(O)—$, however, with the proviso that at least one radical $R^7$, especially at least two radicals $R^7$, does not represent hydrogen.

According to a particular embodiment of the present invention, the reaction product may comprise one or more acyl-capped (acyl-blocked) 3-hydroxybutyric acid polyglycerol esters of the general formula (IIIc)

$$R^7O—CH_2—CH(OR^7)—CH_2—O—CH_2—CH(OR^7)—CH_2—OR^7 \quad \text{(IIIc)}$$

wherein, in the general formula (IIIc), the radical $R^7$, each independently of one another, identical or different, represents: hydrogen or a radical $R^2$, wherein the radical $R^2$ represents a radical $CH_3—C(O)—CH_2—C(O)—$, however, with the proviso that at least one radical $R^7$, especially at least two radicals $R^7$, does not represent hydrogen.

Alternatively, the reaction product (i. e. (chemical) product or product mixture) obtainable according to the inventive method or the inventive reaction product may comprise one or more acyl-capped (acyl-blocked) 3-hydroxybutyric acid polyglycerol esters of the general formula (IIId)

$$R^7O—CH_2—CH(OR^7)—CH_2—OR^7 \quad \text{(IIId)}$$

wherein, in the general formula (IIId), the radical $R^7$, each independently of one another, identical or different, represents: hydrogen or a radical $R^2$, wherein the radical $R^2$ represents a radical $CH_3—C(O)—CH_2—C(O)—$, however, with the proviso that at least one radical $R^7$, especially at least two radicals $R^7$, does not represent hydrogen.

According to a particular embodiment, the reaction product may especially comprise a mixture of at least two different acyl-capped (acyl-blocked) 3-hydroxybutyric acid polyol esters (III), especially 3-hydroxybutyric acid polyglycerol esters, especially as defined hereinabove.

According to a further particular embodiment, the reaction product may especially comprise a mixture of at least three different acyl-capped (acyl-blocked) 3-hydroxybutyric acid polyol esters (III), especially 3-hydroxybutyric acid polyglycerol esters, especially as defined hereinabove.

Especially, the reaction product (i. e. chemical product or product mixture) obtainable according to the inventive method or the inventive reaction product may comprise one or more functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyol esters (III'), especially 3-hydroxybutyric acid polyglycerol esters, of the general formula (IIIa')

$$(R^6O)_m—(X)—(OR^6)_n \quad \text{(IIIa')}$$

wherein, in the general formula (IIIa'),

X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_{21}$-alkyl radical, or a $C_3$-$C_{21}$-(poly)alkyl ether radical, preferentially a $C_4$-$C_{21}$-(poly)alkyl ether radical, especially a $C_3$-$C_{21}$-(poly)alkylene glycol radical, preferentially a $C_4$-$C_{21}$-(poly)alkylene glycol radical, the variables m and n, each independently of one another, represent an integer from 1 to 10, the radical $R^6$, each independently of one another, identical or different, represents: hydrogen or a radical $R^2$, wherein the radical $R^2$ represents a radical $CH—C(O)—CH_2—C(O)—$, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove:

especially wherein the groups $R^6O$—are in any position of the radical X, preferentially wherein at least one group $R^6O$—is terminal.

Especially, in the general formula (IIIa'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove, and with the proviso that at least one radical $R^6$ represents a radical $R^4$, as defined hereinabove.

Especially, it is preferred if, in the general formula (IIIa'), the radical $R^6$, each independently of one another, identical or different, does not represent hydrogen Especially, the reaction product may comprise one or more functionalized, especially fatty acid functionalized, preferentially $C_5$-$C_{33}$-fatty acid functionalized, preferably $C_8$-$C_{34}$-fatty acid functionalized, acyl-capped (acyl-blocked) 3-hydroxybutyric acid polyglycerol esters of the general formula (IIIb')

$$R^6O—CH_2—CH(OR^6)—CH_2—[O—CH_2—CH(OR^6)—CH_2]_p—OR^6 \quad \text{(IIIb)}$$

wherein, in the general formula (IIIb'), the variable p represents an integer from 0 to 6, especially from 1 to 4, preferentially 1 or 2, more preferably 1, the radical $R^6$, each independently of one another, identical or different, represents: hydrogen or a radical $R^2$, wherein the radical $R^2$ represents a radical $CH_3—C(O)—CH_2—C(O)—$, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_1$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove.

Especially, in the general formula (IIIb'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove and with the proviso that at least one radical $R^6$ represents a radical $R^4$ as defined hereinabove.

Especially, it is preferred if, in the general formula (IIIb'), the radical $R^6$, each independently of one another, identical or different, does not represent hydrogen.

According to a particular embodiment of the present invention, the reaction product may comprise one or more functionalized, especially fatty acid functionalized, preferentially $C_5$-$C_{34}$-fatty acid functionalized, preferably $C_8$-$C_{37}$-fatty acid functionalized, acyl-capped (acyl-blocked) 3-hydroxybutyric acid polyglycerol esters of the general formula (IIIc')

$$R^6O—CH_2—CH(OR^6)—CH_2—O—CH_2—CH(OR^6)—CH_2—OR^6 \quad \text{(IIIc')}$$

wherein, in the general formula (IIIc'), the radical $R^6$, each independently of one another, identical or different, represents: hydrogen or a radical $R^{12}$, wherein the radical $R^2$ represents a radical $CH_3—C(O)—CH_2—C(O)—$, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove.

Especially, in the general formula (IIIc'), the radical $R^6$, each independently of one another, identical or different, may represent: a radical $R^2$ as defined hereinabove or a radical $R^4$ as defined hereinabove, however, with the proviso that at least one radical $R^1$, especially at least two radicals $R^6$, represents a radical $R^2$ as defined hereinabove, and with the proviso that at least one radical $R^6$ represents a radical $R^4$ as defined hereinabove.

Especially, it is preferred if, in the general formula (IIIc'), the radical Ra, each independently of one another, identical or different, does not represent hydrogen.

According to an alternative particular embodiment of the present invention, the reaction product may comprise one or more functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyglycerol esters of the general formula (IIId')

$$R^6O—CH_2—CH(OR^6)—CH_2—OR^6 \quad \text{(IIId')}$$

wherein, in the general formula (IIId'), the radical $R^6$, each independently of one another, identical or different, represents: hydrogen or a radical $R^2$, wherein the radical $R^2$ represents a radical $CH_3—C(O)—CH_2—C(O)—$, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_1$-$C_{33}$-alkyl)-C(O)—, however, with the proviso that at least two radicals $R^6$ do not represent hydrogen, ad with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove.

Especially, in the general formula (IIId'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove, and with the proviso that at least one radical $R^6$ represents a radical $R^4$ as defined hereinabove.

It is particularly preferred if, in the general formula (IIId'), the radical $R^6$, each independently of one another, identical or different, does not represent hydrogen.

According to a particular embodiment, the reaction product may especially comprise a mixture of at least two different functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyol esters (III'), especially 3-hydroxybutyric acid polyglycerol esters, especially as defined hereinabove.

According to a further particular embodiment, the reaction product may especially comprise a mixture of at least three different functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyol esters (III'), especially 3-hydroxybutyric acid polyglycerol esters, especially as defined hereinabove.

A subject-matter of the present invention is also an optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyol esters (III"), especially 3-hydroxybutyric acid polyglycerol esters, of the general formula (IIIa")

$(R^6O)_m$—(X)—$(OR^6)$—(IIIa")

wherein, in the general formula (IIIa"),

X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_2$-alkyl radical, or a $C_3$-$C_2$-(poly)alkyl ether radical, preferentially a $C_1$-$C_{21}$-(poly)alkyl ether radical, especially a $C_1$-$C_{21}$-(poly)alkylene glycol radical, preferentially a $C_4$-$C_{21}$-(poly)alkylene glycol radical, the variables m and n, each independently of one another, represent an integer from 1 to 10, the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents a radical $R^2$ as defined hereinabove;

especially wherein the groups $R^6O$—are in any position of the radical X, preferentially wherein at least one group $R^6O$—is terminal.

A further subject-matter of the present invention is also an optionally functionalized acyl-capped (acyl-blocked) 3-hydroxybutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyglycerol ester corresponds to the general formula (IIIb")

$R^6O$—$CH_2$—$CH(OR^6)$—$CH_2$—[O—$CH_2$—CH $(OR^6)$—$CH_2$]—$OR^6$ (IIIb")

wherein, in the general formula (IIIb"), the variable p represents an integer from 0 to 6, especially from 1 to 4, preferentially 1 or 2, more preferably 1, the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially $C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents a radical $R^7$ as defined hereinabove.

Again, another subject-matter of the present invention is also an optionally functionalized acyl-capped (acyl-blocked) 3-hydroxybutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyglycerol ester corresponds to the general formula (IIIC")

$R^6O$—$CH_2$—$CH(OR^6)$—$CH_2$—O—$CH_2$—CH $(OR^6)$—$CH_2$—$OR^6$(IIIc")

wherein, in the general formula (IIIc"), the radical $R^6$, each independently of one another, identical or different, represents: hydrogen or a radical $R^2$, wherein the radical $R^2$ represents a radical $CH_3$—C(O)—$CH_2$—C (O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_1$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^2$, represents a radical $R^2$ as defined hereinabove.

A further subject-matter of the present invention is also an optionally functionalized acyl-capped (acyl-blocked) 3-hydroxybutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyglycerol ester corresponds to the general formula (IIId")

$R^6O$—$CH_2$—$CH(OR^6)$—$CH_2$—$OR^6$(IIId")

wherein, in the general formula (IIId"), the radical $R^6$, each independently of one another, identical or different, represents: hydrogen or a radical $R^2$, wherein the radical $R^2$ represents a radical $CH_3$—C(O)—$CH_2$—C (O)—, or a radical $R^4$, wherein the radical $R^7$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_1$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents a radical $R^2$ as defined hereinabove.

A further subject-matter of the present invention according to this aspect of the invention, according to a particular embodiment, is a mixture comprising at least two different optionally functionalized, preferentially optionally fatty acid functionalized, preferably optionally $C_5$-$C_{33}$-fatty acid functionalized, especially optionally $C_8$-$C_{33}$-fatty acid functionalized, acyl-capped (acyl-blocked) 3-hydroxybutyric acid polyol esters (III"), especially 3-hydroxybutyric acid polyglycerol esters, especially as defined hereinabove.

Again, another subject-matter of the present invention according to this aspect of the invention, according to a particular embodiment, is a mixture comprising at least three different optionally functionalized, preferentially optionally fatty acid functionalized, preferably optionally $C_5$-$C_{34}$-fatty acid functionalized, especially optionally $C_8$-$C_{34}$-fatty acid functionalized, acyl-capped (acyl-blocked) 3-hydroxybutyric acid polyol esters (III"), especially 3-hydroxybutyric acid polyglycerol esters, especially as defined hereinabove.

According to a further embodiment, also a subject-matter of the present invention is an acyl-capped (acyl-blocked) 3-hydroxybutyric acid polyol ester (III), especially 3-hydroxybutyric acid polyglycerol ester, of the general formula (IIIa)

$$(R^7O)_m—(X)—(OR^7) \quad \text{(IIIa)}$$

wherein, in the general formula (IIIa),

X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_{21}$-alkyl radical, or a $C_3$-$C_{21}$-(poly)alkyl ether radical, preferentially a $C_4$-$C_{21}$-(poly)alkyl ether radical, especially a $C_3$-$C_{21}$-(poly)alkylene glycol radical, preferentially a $C_4$-$C_{21}$-(poly)alkylene glycol radical, the variables m and n, each independently of one another, represent an integer from 1 to 10, the radical $R^7$, each independently of one another, identical or different, represents: hydrogen or a radical $R^2$, wherein the radical $R^2$ represents a radical $CH_3$—C(O) $CH_2$—C(O)—, however, with the proviso that at least one radical $R^7$, especially at least two radicals $R^7$, does not represent hydrogen;

especially wherein the groups $R^7O$—are in any position of the radical X, preferentially wherein at least one group $R^7O$—is terminal.

According to this embodiment, another subject-matter of the present invention is an acyl-capped (acyl-blocked) 3-hydroxybutyric acid polyol ester (III), especially as described hereinabove, wherein the acyl-capped (acyl-blocked) 3-hydroxybutyric acid polyglycerol ester corresponds to the general formula (IIIb)

$$R^7O—CH_2—CH(OR^7)—CH_2—[O—CH_2—CH(OR^7)—CH_2]_p—OR^7 \quad \text{(IIIb)}$$

wherein, in the general formula (IIIb), the variable p represents an integer from 0 to 6, especially from 1 to 4, preferentially 1 or 2, and more preferably 1, the radical $R^7$, each independently of one another, identical or different, represents: hydrogen or a radical $R^2$, wherein the radical $R^2$ represents a radical $CH_2$—C(O)—$CH_2$—C(O)—, however, with the proviso that at least one radical $R^7$, especially at least two radicals $R^7$, does not represent hydrogen.

According to this embodiment, an again further subject-matter of the present invention is an acyl-capped (acyl-blocked) 3-hydroxybutyric acid polyol ester (III), especially as described hereinabove, wherein the acyl-capped (acyl-blocked) 3-hydroxybutyric acid polyglycerol ester corresponds to the general formula (IIIc)

$$R^7O—CH_2—CH(OR^7)—CH_2—O—CH_2—CH(OR)—CH_2—OR^7 \quad \text{(IIIc)}$$

wherein, in the general formula (IIIc), the radical $R^7$, each independently of one another, identical or different, represents: hydrogen or a radical $R^2$, wherein the radical $R^2$ represents a radical $CH_3$—C(O)—$CH_2$—C(O)—, however, with the proviso that at least one radical $R^7$, especially at least two radicals $R^7$, does not represent hydrogen.

According to this embodiment, an additional subject-matter of the present invention is an acyl-capped (acyl-blocked) 3-hydroxybutyric acid polyol ester (ill), especially as described hereinabove, wherein the acyl-capped (acyl-blocked) 3-hydroxybutyric acid polyglycerol ester corresponds to the general formula (IIId)

$$R^7O—CH_2—CH(OR^7)—CH_2—OR^7 \quad \text{(IIId)}$$

wherein, in the general formula (IIId), the radical $R^7$, each independently of one another, identical or different, represents: hydrogen or a radical $R^2$, wherein the radical $R^2$ represents a radical $CH_3$—C(O)—$CH_2$—C(O)—, however, with the proviso that at least one radical $R^7$, especially at least two radicals $R^7$, does not represent hydrogen.

Another subject-matter of the present invention according to this aspect of the invention according to a further particular embodiment is a mixture comprising at least two different acyl-capped (acyl-blocked) 3-hydroxybutyric acid polyol esters (III), especially 3-hydroxybutyric acid polyglycerol esters, especially as defined hereinabove.

An again further subject-matter of the present invention according to this aspect of the invention according to a further particular embodiment is a mixture comprising at least three different acyl-capped (acyl-blocked) 3-hydroxybutyric acid polyol esters (iii), especially 3-hydroxybutyric acid polyglycerol esters, especially as defined hereinabove.

According to a further alternative embodiment, also a subject-matter of the present invention is a functionalized, especially fatty acid functionalized, preferentially $C_5$-$C_{34}$ fatty acid functionalized, preferably $C_8$-$C_{34}$ fatty acid functionalized, acyl-capped (acyl-blocked) 3-hydroxybutyric acid polyol ester (III), especially 3-hydroxybutyric acid polyglycerol ester, of the general formula (IIIa')

$$(R^6O)_m—(X)—(OR^6)_n \quad \text{(IIIa')}$$

wherein, in the general formula (IIIa'),

X represents an organic radical, especially a preferentially saturated organic radical comprising 3 to 21 carbon atoms, preferentially 4 to 21 carbon atoms, and optionally comprising 1 to 9 oxygen atoms, preferentially selected from an alkyl radical or a (poly)alkyl ether radical, especially a (poly)alkylene glycol radical, more preferably selected from a $C_3$-$C_{21}$-alkyl radical, preferentially a $C_4$-$C_{21}$-alkyl radical, or a $C_3$-$C_{21}$-(poly)alkyl ether radical, preferentially a $C_4$-$C_{21}$-(poly)alkyl ether radical, especially a $C_3$-$C_{21}$-(poly)alkylene glycol radical, preferentially a $C_4$-$C_{21}$-(poly)alkylene glycol radical, the variables m and n, each independently of one another, represent an integer from 1 to 10, the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_3$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals Rb, represents a radical $R^4$ as defined hereinabove;

especially wherein the groups $R^6$O—are in any positions of the radical X, preferentially wherein at least one group $R^6$O—is terminal.

Especially, in the general formula (IIIa'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove, and with the proviso that at least one radical $R^6$ represents a radical $R^4$ as defined hereinabove.

In this particular embodiment, it is advantageous if, in the general formula (IIIa'), the radical $R^6$, each independently of one another, identical or different, does not represent hydrogen.

According to this particular embodiment, another subject-matter of the present invention is functionalized acyl-capped (acyl-blocked) 3-hydroxybutyric acid polyol ester (III'), especially as described hereinabove, wherein the functionalized, especially fatty acid functionalized, preferentially $C_5$-$C_{34}$-fatty acid functionalized, preferably $C_8$-$C_{37}$-fatty acid functionalized, acyl-capped (acyl-blocked) 3-hydroxybutyric acid polyglycerol ester corresponds to the general formula (IIIb')

$$R^6O—CH_2—CH(OR^6)—CH_2[O—CH_2—CH(OR^6)—CH_2]_p—OR^6 \quad \text{(IIIb')}$$

wherein, in the general formula (IIIb'), the variable p represents an integer from 0 to 6, especially from 1 to 4, preferentially 1 or 2, more preferably 1, the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^1$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove.

Especially, in the general formula (IIIb'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove, and with the proviso that at least one radical $R^6$ represents a radical $R^4$ as defined hereinabove.

In this particular embodiment, it is preferred if, in the general formula (IIIb'), the radical $R^6$, each independently of one another, identical or different, does not represent hydrogen.

According to this particular embodiment, another subject-matter of the present invention is a functionalized acyl-capped (acyl-blocked) 3-hydroxybutyric acid polyol ester (III'), especially as described hereinabove, wherein the functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyglycerol ester corresponds to the general formula (IIIc')

$$R^6O—CH_2—CH(OR^6)—CH_2—O—CH_2—CH(OR^6)—CH_2—OR^6 \quad \text{(IIIc')}$$

wherein, in the general formula (IIIc'), the radical $R^6$, each independently of one another, identical or different, represents: hydrogen or a radical $R^2$, wherein the radical $R^2$ represents a radical $CH_3$—C(O)—$CH_2$—C(O)—, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove.

Especially, in the general formula (IIIc'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove, and with the proviso that at least one radical $R^6$ represents a radical $R^4$ as defined hereinabove.

In this particular embodiment, it is preferred if, in the general formula (IIIc'), the radical $R^6$, each independently of one another, identical or different, does not represent hydrogen.

According to this particular embodiment, an again further subject-matter of the present invention is a functionalized acyl-capped (acyl-blocked) 3-hydroxybutyric acid polyol ester (III'), especially as described hereinabove, wherein the functionalized, especially fatty acid functionalized, preferentially $C_5$-$C_{34}$ fatty acid functionalized, preferably $C_8$-$C_{34}$ fatty acid functionalized, acyl-capped (acyl-blocked) 3-hydroxybutyric acid polyglycerol ester corresponds to the general formula (IIId')

$$R^6O—CH_2—CH(OR^6)—CH_2—OR^6 \quad \text{(IIId')}$$

wherein, in the general formula (IIId') the radical $R^6$, each independently of one another, identical or different, represents: hydrogen or a radical $R^2$, wherein the radical $R^2$ represents a radical $CH_3—C(O)—CH_2—C(O)—$, or a radical $R^4$, wherein the radical $R^4$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferentially ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents a radical $R^2$ as defined hereinabove, and with the proviso that at least one radical $R^6$, especially at least two radicals $R^6$, represents a radical $R^4$ as defined hereinabove.

Especially, in the general formula (IIId'), the radical $R^6$, each independently of one another, identical or different, may represent: a radical $R^2$ as defined hereinabove or a radical $R^4$ as defined hereinabove, however, with the proviso that at least one radical $R^6$, especially at least two radicals $R^6$, represents a radical $R^2$ as defined hereinabove, and with the proviso that at least one radical $R^6$ represents a radical $R^4$ as defined hereinabove.

In this particular embodiment, it is preferred if, in the general formula (IIId'), the radical $R^6$, each independently of one another, identical or different, does not represent hydrogen.

A further subject-matter of the present invention according to this aspect of the invention is, according to a further particular embodiment, a mixture comprising at least two different functionalized, especially fatty acid functionalized, preferentially $C_5$-$C_{34}$-fatty acid functionalized, preferably $C_3$-$C_{34}$-fatty acid functionalized, acyl-capped (acyl-blocked) 3-hydroxybutyric acid polyol esters (III'), especially 3-hydroxybutyric acid polyglycerol esters, especially as defined hereinabove.

Again, another subject-matter of the present invention according to this aspect of the invention is, according to a further particular embodiment, a mixture comprising at least three different functionalized, especially fatty acid functionalized, preferentially $C_5$-$C_{34}$-fatty acid functionalized, preferably $C_8$-$C_{34}$-fatty acid functionalized, acyl-capped (acyl-blocked) 3-hydroxybutyric acid polyol esters (III'), especially 3-hydroxybutyric acid polyglycerol esters, especially as defined hereinabove.

As the applicant has surprisingly found out, the reaction product obtainable according to the inventive method or the inventive reaction product as defined hereinabove, respectively, and/or the optionally functionalized polyol ester, especially polyglycerol ester, of acyl-capped (acyl-blocked) 3-hydroxybutyric acid obtainable according to the inventive production method or the inventive optionally functionalized polyol ester, especially polyglycerol ester, of acyl-capped (acyl-blocked) 3-hydroxybutyric acid, as defined hereinabove, respectively, and/or the mixture, obtainable according to the inventive production method or the inventive mixture as defined hereinabove, respectively, is suitable as a precursor or metabolite of 3-hydroxybutyric acid or its salts, since, on the one hand, it is converted physiologically, especially in the gastrointestinal tract, to the keto bodies 3-hydroxybutyric acid and 3-oxobutyrate (=acetoacetate or acetacetate), which is physiologically ultimately converted or reduced to 3-hydroxybutyric acid or its salts, and, on the other hand, it simultaneously comprises a good physiological compatibility or tolerability, especially with regard to non-toxicity and acceptable organoleptic properties. Especially, the sustained release of the physiologically active substance in the gastrointestinal tract is advantageous in the medical field, since the active substance 3-hydroxybutyric acid can thus be made available over a longer period of time, thus enabling ketosis therapy.

Therefore, the reaction product obtainable according to the inventive method or the inventive reaction product as defined hereinabove, respectively, and/or the optionally functionalized polyol ester, especially polyglycerol ester, of acyl-capped (acyl-blocked) 3-hydroxybutyric acid obtainable according to the inventive production method or the inventive optionally functionalized polyol ester, especially polyglycerol ester, of acyl-capped (acyl-blocked) 3-hydroxybutyric acid as defined hereinabove, respectively, and/or the mixture, obtainable according to the inventive production method or the inventive mixture as defined hereinabove, respectively, are suitable as effective precursors or metabolites which physiologically provide direct or indirect access to 3-hydroxybutyric acid or its salts and to acetoacetate (and thus physiologically in turn to 3-hydroxybutyric acid or its salts), especially in the physiological metabolism of the human or animal body.

Thus, during the physiological cleavage in the stomach and/or intestine, the reaction product obtainable according to the inventive method or the inventive reaction product as defined hereinabove, respectively, and/or the optionally functionalized polyol ester, especially polyglycerol ester, of acyl-capped (acyl-blocked) 3-hydroxybutyric acid obtainable according to the inventive production method or the inventive optionally functionalized polyol ester, especially polyglycerol ester, of acyl-capped (acyl-blocked) 3-hydroxybutyric acid as defined hereinabove, respectively, and/or the mixture, obtainable according to the inventive production method or the inventive mixture as defined hereinabove, respectively, is cleaved into the keto compounds 3-hydroxybutyric acid and 3-oxobutyrate (acetoacetate and acetacetate, respectively), which can be further reduced by the body to 3-hydroxybutyrate.

Due to the presence of both 3-oxobutyrate radicals and 3-hydroxybutyrate radicals or 3-hydroxybutyric acid, there is a different rate of availability or release of the active ingredient 3-hydroxybutyric acid. Consequently, the inventive reaction product has an intrinsic, further differentiated retard effect. For, overall, the inventive optionally functionalized polyol ester, especially polyglycerol ester, of acyl-capped (acyl-blocked) 3-hydroxybutyric acid or its salt or ester thus exhibits two keto bodies with different rates of degradation. There is also an additional or further retardation since the keto bodies are present in the form of a polyol ester and therefore the active ingredients 3-hydroxybutyric acid in free form and acetoacetate must also be split off from the polyol. Overall, the active ingredients 3-hydroxybutyric acid and acetoacetate are released from the inventive optionally functionalized polyol ester, especially polyglycerol ester, of acyl-capped (acyl-blocked) 3-hydroxybutyric acid by a multi-stage degradation with a retardation effect The inventive method thus makes it possible for the first time to provide non-toxic, optionally functionalized polyol esters, especially polyglycerol esters, of acyl-capped (acyl-blocked) 3-hydroxybutyric acid from components or reactants (starting compounds) which are known per se, commercially available and, above all, physiologically harmless. The resulting optionally functionalized polyol esters, especially polyglycerol esters, of acyl-capped 3-hydroxybutyric acid can be physiologically cleaved, especially in the stomach and/or in the intestine, and release or generate the target molecule “3-hydroxybutyric acid” or its salts as active ingredient or active component. At the same time, the further keto body acetoacetate is also physiologically released from the acyl-capping of 3-hydroxybutyric acid (which is then further reduced to 3-hydroxybutyric acid).

Moreover, the reaction product obtainable according to the inventive method or the inventive reaction product as defined hereinabove, respectively, and/or the optionally functionalized polyol ester, especially polyglycerol ester, of acyl-capped (acyl-blocked) 3-hydroxybutyric acid, obtainable according to the inventive production method or the inventive optionally functionalized polyol ester, especially polyglycerol ester, of acyl-capped (acyl-blocked) 3-hydroxybutyric acid, as defined hereinabove, respectively, and/or the mixture, obtainable according to the inventive production method or the inventive mixture as defined hereinabove, respectively, is easily accessible or available on a large scale on a synthetic basis, even on a commercial scale, and with the required pharmaceutical or pharmacological quality.

Additionally, the reaction product obtainable according to the inventive method or the inventive reaction product as defined hereinabove, respectively, and/or the optionally functionalized polyol ester, especially polyglycerol ester, of acyl-capped (acyl-blocked) 3-hydroxybutyric acid as defined hereinabove, respectively, and/or the mixture, obtainable according to the inventive production method or the inventive mixture as defined hereinabove, respectively, can, if necessary, be provided in enantiomerically pure or enantiomerically enriched form.

The reaction product obtainable according to the inventive method or the inventive reaction product as defined hereinabove, respectively, and/or the optionally functionalized polyol ester, especially polyglycerol ester, of acyl-capped (acyl-blocked) 3-hydroxybutyric acid, obtainable according to the inventive production method or the inventive optionally functionalized polyol ester, especially polyglycerol ester, of acyl-capped (acyl-blocked) 3-hydroxybutyric acid as defined hereinabove, respectively, and/or the mixture, obtainable according to the inventive production method or the inventive mixture as defined hereinabove, respectively, thus represents an efficient pharmacological drug target in the context of keto-body therapy of the human or animal body.

The remaining aspects of the invention will be further explained and described in detail below.

A further subject-matter of the present invention—according to a fourth aspect of the present invention—is a pharmaceutical composition, especially a drug or medicament, which comprises a reaction product obtainable according to the inventive production method or the inventive reaction product as defined hereinabove, respectively, and/or an optionally functionalized polyol ester, especially polyglycerol ester, of acyl-capped (acyl-blocked) 3-hydroxybutyric acid, obtainable according to the inventive production method or the inventive optionally functionalized polyol ester, especially polyglycerol ester, of acyl-capped (acyl-blocked) 3-hydroxybutyric acid as defined hereinabove, respectively, and/or a mixture, obtainable according to the inventive production method or the inventive mixture as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer’s disease, Parkinson’s disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington’s disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn’s disease, lyosomal storage diseases such as sphingolipidosis, especially Niemann-Pick disease, diabetes mellitus and effects or side-effects of chemotherapy.

Again, a further subject-matter of the present invention—according to a fifth aspect of the present invention—is a reaction product obtainable according to the inventive production method or the inventive reaction product as defined hereinabove, respectively, and/or an optionally functionalized polyol ester, especially polyglycerol ester, of acyl-capped (acyl-blocked) 3-hydroxybutyric acid, obtainable according to the inventive production method or the inventive optionally functionalized polyol ester, especially polyglycerol ester, of acyl-capped (acyl-blocked) 3-hydroxybutyric acid as defined hereinabove, respectively, and/or a mixture, obtainable according to the inventive production method or the inventive mixture as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer’s disease, Parkinson’s disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington’s disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn’s disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product as defined hereinabove, respectively, and/or use of an optionally functionalized polyol ester, especially polyglycerol ester, of acyl-capped (acyl-blocked) 3-hydroxybutyric acid as defined hereinabove, respectively, and/or use of a mixture as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflamatory bowel diseases, especially ulcerative colitis and Crohn's disease, lysosomal storage diseases such as sphingolipidosis, especially Niemann-Pick disease, diabetes mellitus and effects or side-effects of chemotherapy.

Likewise, a further subject-matter of the present invention—according to a seventh aspect of the present invention—is the use of a reaction product obtainable according to the inventive production method or the inventive reaction product as defined hereinabove, respectively, and/or use of an optionally functionalized polyol ester, especially polyglycerol ester, of acyl-capped (acyl-blocked) 3-hydroxybutyric acid, obtainable according to the inventive production method or the optionally functionalized polyol ester, especially polyglycerol ester, of acyl-capped (acyl-blocked) 3-hydroxybutyric acid as defined hereinabove, respectively, and/or use of a mixture, obtainable according to the inventive production method or the inventive mixture as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a eighth aspect of the present invention—is a food and/or a food product, which comprises a reaction product obtainable according to the inventive production method or the inventive reaction product as defined hereinabove, respectively, and/or an optionally functionalized polyol ester, especially polyglycerol ester, of acyl-capped (acyl-blocked) 3-hydroxybutyric acid, obtainable according to the inventive production method or the inventive optionally functionalized polyol ester, especially polyglycerol ester, of acyl-capped (acyl-blocked) 3-hydroxybutyric acid as defined hereinabove, respectively, and/or a mixture, obtainable according to the inventive production method or the inventive mixture as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an ninth aspect of the present invention—is the use of a reaction product obtainable according to the inventive production method or the inventive reaction product as defined hereinabove, respectively, and/or an optionally functionalized polyol ester, especially polyglycerol ester, of acyl-capped (acyl-blocked) 3-hydroxybutyric acid, obtainable according to the inventive production method or the inventive optionally functionalized polyol ester, especially polyglycerol ester, of acyl-capped (acyl-blocked) 3-hydroxybutyric acid as defined hereinabove, respectively, and/or a mixture, obtainable according to the inventive production method or the inventive mixture as defined hereinabove, respectively, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

Examples

Abbreviations Used

3-BHB=3-hydroxybutyric acid or 3-hydroxybutyric acid radical (3-hydroxybutyrate radical)

3-BHB-FS=3-hydroxybutyric acid (free acid)

PG(2)=diglycerol: $HO—CH_2—CH(OH)—CH_2—O—CH_2—CH(OH)—CH_2—OH$

PG(3)=polyglycerol: $HO—CH_2—CH(OH)—CH_2$µ-[$O—CH_2—CH(OH)—CH_2]_2$ µOH

3-BHB dimer ethyl ester=dimer of 3-BHB ethyl ester 3-acetylaceto-$BHB_2$ ethyl ester=dimer of 3-BHB ethyl ester capped with ethyl acetoacetate

Examples of Production

The inventive production method is illustrated by the following examples. The relevant general reaction scheme is shown and explained in the general description section.

Production of 3-acetylacetobutyric acid diglycerol ester Mixtures

In a 100-ml-multi-neck flask with dephlegmator (partial condenser) and distillation bridge, 89 g 3-acetylacetobutyric acid ethyl ester (3-acetylaceto-BHB-ethyl ester), 3.5 g diglycerol and 0.9 g immobilized enzyme (CALB-lipase on polymer support, derived from *Candida antarctica*, e. g. Novozym® 435) are provided.

The reaction mixture is reacted at 50° C. to 70° C. under vacuum and stirring for 6 h. The ethanol produced is continuously distilled off. The enzyme is then filtered off and excess 3-acetylacetobutyric acid ethyl ester is distilled off under vacuum. A mixture of mono-, di-, tri- and tetra-diglycerol esters of 3-acetylacetobutyric acid is obtained. Characterization is performed by gas chromatography (CC), gel permeation chromatography (GPC) and GC-MS analysis (gas chromatography with mass spectrometry coupling).

In the course of purification, any reactants still present and any reaction by-products present are removed so that a pure mixture is obtained. Part of the mixture is subjected to separation by chromatography so that the various diglycerol esters are each obtained as pure substances (i. e. pure 3-acetylacetobutyric acid mono-diglycerol ester, pure 3-acetylacetobutyric acid di-diglycerol ester, pure 3-acetylacetobutyric acid tri-diglycerol ester and pure 3-acetylacetobutyric acid tetra-diglycerol ester). Another part of the mixture is subjected to fractional distillation separation.

Further production of 3-acetylacetobutyric acid diglycerol esters

In a 100-ml-multi-neck flask with dephlegmator (partial condenser) and distillation bridge, 178 g 3-acetylacetobutyric acid ethyl ester (3-acetylaceto-BHB-ethyl ester) and 29 g diglycerol are provided.

At a temperature of 100° C., 1.4 g of 30% methanolic NaOMe solution is added under stirring. The ethanol produced is continuously distilled off. After a reaction time of 5 h, the reaction mixture is cooled and washed with NaCl solution. The crude ester mixture is then dried and the excess 3-acetylacetobutyric acid ethyl ester is distilled off under vacuum.

The reaction product is a 3-acetylacetobutyric acid diglycerol ester mixture with the following composition: 3-acetylacetobutyric acid mono-diglycerol ester, 3-acetylacetobutyric acid di-diglycerol ester, 3-acetylacetobutyric acid tri-diglycerol ester and 3-acetylacetobutyric acid tetra-diglycerol ester. The characterization is performed by GC, GPC and GC-MS.

In the course of purification, reactants and reaction by-products are removed so that a pure mixture is obtained. Part of the mixture is subjected to separation by chromatography so that the various diglycerol esters are each obtained as pure substances (i. e. pure 3-acetylacetobutyric acid mono-diglycerol ester, pure 3-acetylacetobutyric acid di-diglycerol ester, pure 3-acetylacetobutyric acid tri-diglycerol ester, etc.). Another part of the mixture is subjected to separation by fractional distillation.

Further Production of acyl-Capped 3-BHB polyol esters

The preceding experiments are each repeated (with enzyme and with NaOMe as catalyst), however, with different polyols (namely with glycerol, polyglycerol PG(3) and 1,2-pentanediol). Comparable results are obtained. Purification and fractionation are performed in the same way.

Again More Production Examples

Various polyol components based on polyhydric alcohols (polyols) are enzymatically reacted with 3-acetylacetobutyric acid ethyl esters. 1,2-pentanediol and diglycerol PG(2) are selected as polyols. The respective polyols are reacted at 70° C. for 24 h with immobilized enzyme (CALB lipase on polymer support, derived from *Candida antarctica*, e. g. Novozym® 435 from Sigma-Aldrich or Merck or Lipozym® 435 from Strem Chemicals, Inc.) (in each case 1% by weight enzyme and in each case 40 mol-% excess 3-acetylacetobutyric acid ethyl ester).

The aforementioned polyols 1,2-pentanediol and diglycerol PG(2) are efficiently reacted with the aforementioned enzymes to give the desired products. Comparable results to the previous experiments are obtained. Purification and separation or fractionation are carried out in the same way.

The experiments are repeated using sodium methanolate (NaCMe) as catalyst instead of the enzymes and at temperatures between 10° and 120° C. Comparable results are obtained. Purification and separation or fractionation are carried out in the same way.

Since especially the 3-acetylacetobutyric acid PG(2) esters only have a slightly bitter taste, these esters are especially an efficient product group for a therapeutic application. Therefore, the preceding experiment with enzyme and diglycerol PG(2) as polyol is carried out on a larger scale (2 to 4 kg).

First, the stoichiometric reaction conditions of the previous experiments are applied in a scale of 2 kg (40 mol-% excess 3-acetylacetobutyric acid ethyl ester, 1% by weight enzyme). After 15 h, a portion of the reaction mixture (about 200 g) is removed for further analysis. This is a mono/di-PG(2) ester mixture. Then another approximately 1 kg of 3-acetylacetobutyric acid ethyl ester is added. The aim is to produce a full ester. It can be seen that after about 20 to 30 h a constant content of di-PG(2)-ester is obtained; the mono-PG(2)-ester content decreases and the tri-PG(2)-ester content increases. Further analyses (GPC) show that a tetra-PG(2)-ester was also formed.

After distilling off excess 3-acetylacetobutyric acid ethyl ester, the initially obtained (low-boiling) mono/di-PG(2) ester mixture exhibits only a slightly bitter taste, while the higher (higher-boiling) di/tri/tetra-PG(2) ester mixture exhibits a somewhat more bitter taste. However, both mixtures are organoleptically acceptable and compatible.

After further purification with removal of residual reactants and reaction by-products, a pure mixture with significantly improved organoleptic properties is obtained.

Functionalization Attempts

1. Production of the anhydride

In a 2,000-ml-multi-neck flask with dephlegmator (partial condenser) and distillation bridge, 860 g heptanoic acid are provided and 445 g acetic anhydride are added at 90° C. under stirring. The reaction mixture is stirred at 130° C. under reflux for 6 h. The resulting acetic acid and the excess acetic anhydride are then distilled off tinder vacuum. A heptanoic acid/heptanoic anhydride mixture is obtained with the following composition: 15% heptanoic acid, 85% heptanoic anhydride. The characterization is performed by GC and GC-MS.

2. Functionalization

In a 100-mil-multi-neck flask equipped with a dephlegmator (partial condenser) and distillation bridge, 25 g heptanoic anhydride and 5 g of a 3-acetylaceto-BHB mono-, di-, tri-, tetra-diglycerol mixture prepared according to the invention are provided. The reaction mixture is stirred at 70° C. for 24 h. Thereafter, excess heptanoic anhydride and the resulting heptanoic acid are distilled off by short path distillation. A 3-acetylaceto-BHB/heptanoic acid diglycerol ester mixture is obtained (i. e. in other words, a 3-acetylaceto-BHB-diglycerol ester mixture heptanoic acid functionalized or esterified at the free OH-groups).

Comparable functionalization experiments are also carried out with fatty acids and alternatively fatty acid anhydrides and again alternatively fatty acid esters (each with eicosapentaenoic acid/docosahexaenoic acid mixture and their anhydrides and esters on the one hand and with oleic acid and its anhydride and ester on the other hand) and each lead to analogous results (i. e. esterification of the free OH-groups), as confirmed by corresponding analytics.

The experiments show that the intended functionalization (esterification) by reaction with carboxylic acids and alternatively carboxylic acid anhydrides and again alternatively carboxylic acid esters leads to the desired products (i. e. esterification of the free OH-groups), as confirmed by corresponding analytics.

Further syntheses of functionalized 3-acetylaceto-BHB polyol esters

The polyols used are 1,2-pentanediol and diglycerol PG(2). The respective polyols are first reacted with sodium methanolate (NaOMe) as a catalyst and at temperatures between 10° and 120° C. with fatty acids and alternatively fatty acid anhydrides and again alternatively fatty acid esters (each with eicosapentaenoic acid, docosahexaenoic acid and oleic acid and their anhydrides and esters); the corresponding fatty acid esterified polyols result, which are further reacted with 3-acetylaceto-BHB ethyl esters in a second, subsequent method step. The corresponding 3-acetylaceto-BHB/fatty acid polyol ester mixtures result. Comparable results are obtained by the reverse procedure (i. e. first reaction of the polyols with ethyl 3-oxobutyric acid ester, followed by further reaction with the aforementioned fatty acids or alternatively their anhydrides and esters).

Production of 3-acetylaceto-BB ethyl ester (=Reactant)

52 g ethyl 3-oxobutyric acid ester (ethyl acetoacetate or acetoacetic acid ester) and 26 g ethyl 3-hydroxybutyric acid ester are provided in a 100-ml-multi-neck flask with dephlegmator (partial condenser) and distillation bridge.

At a temperature of 50° C. and under vacuum, 0.8 g immobilized enzyme (CALB lipase on polymer support, derived from *Candida antarctica*, e. g. Novozym® 435) is added. The reaction mixture is allowed to react for 6 h under stirring. The ethanol produced during the reaction is continuously distilled off. Subsequently, the enzyme is filtered off and excess 3-oxobutyric acid ethyl ester as well as excess 3-hydroxybutyric acid ethyl ester is distilled off under vacuum and recycled.

The reaction product obtained is a 3-acetylacetobutyric acid ethyl ester (3-acetylaceto-BHB ethyl ester) and, after analytical examination, consists of the following composition: >90% 3-acetylaceto-BHB ethyl ester (reaction by-products: 3-BHB dimer ethyl ester <5% and acetylaceto-BHB dimer ethyl ester <5%). Distillative purification leads to pure 3-acetylacetobutyric acid ethyl esters (purity >99.9%). Characterization is performed by GC and GC-MS.

Further production of 3-acetylaceto-BHB-ethyl ester (=Reactant)

30 g ethyl 3-oxobutyric acid ester (ethyl acetoacetate or acetoacetic acid ester) and 15.25 g ethyl 3-hydroxybutyric acid ester (ethyl 3-BHB ester) are provided in a 100-ml-multi-neck flask equipped with a dephlegmator (partial condenser) and a distillation bridge.

At a temperature of 50° C. and under vacuum, 0.46 g immobilized enzyme (CALB lipase on polymer support, derived from *Candida antarctica*, e. g. Novozym® 435) is added. The reaction mixture is allowed to react for 6 h under stirring. The ethanol produced during the reaction is continuously distilled off. The enzyme is then filtered off and excess ethyl 3-oxobutyric acid ester and excess ethyl 3-hydroxybutyric acid ester are distilled off under vacuum and then recycled.

The characterization is performed by GC and GC-MS.

Again, Further Examples of the Production of 3-acetlaceto-BHB-ethyl ester (=Reactant)

In a further series of experiments, the influence of the molar ratio of the starting compounds is investigated with regard to the formation of by-products (analytically examined using the two by-products "3-BHB dimer ethyl ester" and "acetylaceto-$BHB_2$ ethyl ester").

It is shown that a molar excess of 3-oxobutyric acid ethyl ester (ethyl acetoacetate or acetoacetic ester) in relation to the other reactant 3-hydroxybutyric acid ethyl ester (3-BHB ethyl ester) counteracts by-product formation.

In a first series of investigations, an acetoacetic ester/3-BHB ethyl ester molar ratio in the range of 1.5:1 to 9:1 is shown to be particularly efficient in terms of by-product formation and is also still process economical. Particularly good results are observed in a second series of investigations for an acetoacetic ester/3-BHB ethyl ester molar ratio in the range from 2:1 to 8:1.

Physiological Application Tests: In-Vitro Digestion Tests

Digestion Experiments (Splitting or Cleavage Experiments) of Inventive acyl-Capped 3-hydroxybutyric acid PG(2) ester Mixtures By means of cleavage experiments, it is shown that acyl-capped 3-hydroxybutyric acid PG(2) esters or mixtures thereof prepared according to the invention, as well as their functionalized derivatives (i. e. esterified at three OH-groups) including the reaction by-products, can be cleaved in the human gastrointestinal tract.

The starting mixture used is, on the one hand, a purified mixture of 3-acetylaceto-BHB mono-diglycerol ester, 3-acetylaceto-BHB di-diglycerol ester, 3-acetylaceto-BHB tri-diglycerol ester and 3-acetylaceto-BHB tetra-diglycerol ester obtained by the method according to the invention and, on the other hand, a purified, mixture of functionalized 3-acetylaceto-BHB mono-diglycerol ester, functionalized 3-acetylaceto-BHB di-diglycerol ester and functionalized 3-acetylaceto-BHB tri-diglycerol ester obtained by the method according to the invention (functionalization with heptanoic acid or oleic acid or eicosapentaenoic acid/docosahexaenoic acid mixtures).

For the cleavage experiments under near-body conditions two media are investigated:

FaSSGF, which simulates the stomach

FaSSIF, which simulates the intestinal tract

Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that the samples hydrolyze under FaSSGF conditions with Panzytrat® and without Panzytrat®; this is mainly due to the low pH value (pH=1.6) of the medium. Under FaSSIF conditions, a lower conversion using Panzytrat® takes place.

The experiments prove that the 3-acetylaceto-BHB diglycerol esters as well as their functionalized derivatives each represent a suitable physiological precursor for the keto bodies 3-hydroxybutyric acid as well as acetoacetate (and thereby ultimately 3-hydroxybutyric acid again) for use in the corresponding keto body therapies.

Further Digestion Experiments (Cleavage Experiments) of Inventive acyl-Capped 3-hydroxybutyric acid PG(2) ester Mixtures Cleavage Experiments with Pancreatin 3.5 g of each 3-acetylaceto-BHB mono-diglycerol ester, 3-acetylaceto-BHB di-diglycerol ester, 3-acetylaceto-BHB tri-diglycerol ester and 3-acetylaceto-BHB tetra-diglycerol ester prepared as described hereinabove on the one hand and a purified, mixture of functionalized 3-acetylaceto-BHB mono-diglycerol ester, functionalized 3-acetylaceto-BHB di-diglycerol ester and functionalized 3-acetylaceto-BHB tri-diglycerol ester obtained by the method according to the invention on the other hand are dissolved in 50 g water and mixed with 0.5 g (1% by weight) pancreatin. The pancreatin is used in the form of the commercially available product Panzytrat® 40,000 from the Allergan company. The whole mixture is stirred on a hotplate at 50° C.; the course of the reaction is determined and followed by continuous recording of the acid number over time. The acid number increases over the observation period (cleavage of the 3-acetylaceto-BHB-diglycerol ester mixture to the free 3-hydroxybutyric acid and acetoacetate, which can be physiologically reduced to 3-BHB or to 3-hydroxybutyrate, respectively). The conversion/time course of the aqueous cleavage of the esters according to the invention by means of pancreatin, including increase of the acid number over time, proves the desired decomposition of the reactant or reactant mixture to the free acid. This is confirmed by corresponding analytics. The experiment proves that both the 3-acetylaceto-BHB diglycerol ester according to the invention and the functionalized derivatives are suitable physiological precursors for 3-hydroxybutyric acid for the corresponding keto body therapies. The experiments are repeated and verified using each ester in its pure form. Comparable results are obtained, i. e. both the 3-acetylaceto-BHB diglycerol esters and the functionalized derivatives are each cleaved by pancreatin.

The previously described cleavage experiments prove that the polyol esters, especially polyglycerol esters, of acyl-capped 3-hydroxybutyric acid are efficient precursors or metabolites of free 3-hydroxybutyric acid or its salts, especially with regard to their intended effect, which are present in physiologically tolerable or physiologically compatible form.

Further Digestion Experiments (Cleavage Experiments) of Further Inventive 3-acetylaceto-BHB polyol ester Mixtures In addition, the other polyol ester mixtures of 3-acetylacetobutyric acid prepared according to the invention are also subjected to digestion experiments in an appropriate manner, as described above, and deliver analogous results.

The cleavage experiments also demonstrate that the remaining polyol esters of 3-acetylacetobutyric acid are efficient precursors or metabolites for the keto bodies 3-hydroxybutyric acid and acetoacetate for use in the corresponding keto body therapies, especially with respect to their intended effects, which are also present in physiologically tolerable or physiologically compatible forms.

The invention claimed is:

1. A polyglycerol ester of an acetoacetyl-capped 3-hydroxybutyric acid according to general formula (IIIb")

$$R^6O—CH_2—CH(OR^6)—CH_2—[O—CH_2—CH(OR^6)—CH_2]_p—OR^6 \quad \text{(IIb")}$$

wherein, in the general formula (IIIb"), the variable p represents an integer from 1 to 4, the radical $R^6$, each independently of one another, identical or different, represents: hydrogen or a radical $CH_3$-$CH(OR^2)$-$CH_2$-C(O)-, wherein the radical $R^2$ represents a radical $CH_3$-C(O)-$CH_2$-C(O)- or a radical $R^4$, wherein the radical $R^4$ represents a radical of the type linear or branched, saturated or mono-or polyunsaturated ($C_1$-$C_{33}$-alkyl)-C(O)-, however, with the proviso that at least one radical $R^6$ does not represent hydrogen, and with the proviso that at least one radical $R^6$ represents a radical $CH_3$-$CH(OR^2)$-$CH_2$-C(O)-.

2. The polyglycerol ester of an acetoacetyl-capped 3-hydroxybutyric acid according to claim 1, wherein the polyglycerol ester of an acetoacetyl-capped 3-hydroxybutyric acid corresponds to general formula (IIIc")

$$R^6O—CH_2—CH(OR^6)—CH_2—O—CH_2—CH(OR^6)—CH_2—OR^6 \quad \text{(IIIc")}$$

wherein, in the general formula (IIIc"), the radical $R^6$, each independently of one another, identical or different, represents: hydrogen or a radical $CH_3$-$CH(OR^2)$-$CH_2$-C(O)-, wherein the radical $R^2$ represents a radical $CH_3$-C(O)-$CH_2$-C(O)-or a radical $R^4$, wherein the radical $R^4$ represents a radical of the type linear or branched, saturated or mono-or polyunsaturated ($C_1$-$C_{33}$-alkyl)-C(O)-, however, with the proviso that at least one radical $R^6$ does not represent hydrogen, and with the proviso that at least one radical $R^6$ represents a radical $CH_3$-$CH(OR^2)$-$CH_2$-C(O)-.

3. A mixture comprising at least two different polyglycerol esters of an acetoacetyl-capped of 3-hydroxybutyric acid according to claim 1.

4. A pharmaceutical composition comprising at least one polyglycerol ester of an acetoacetyl-capped 3-hydroxybutyric acid according to claim 1.

5. The pharmaceutical composition according to claim 4, wherein the pharmaceutical composition is a drug or medicament.

6. A method for treating a human or an animal suffering from a disease of the human or animal body, wherein the method comprises the administration of an efficient amount of at least one polyglycerol ester of an acetoacetyl-capped 3-hydroxybutyric acid according to claim 1.

7. The method of claim 6, wherein the disease is selected among diseases associated with a disorder of the energy metabolism or diseases associated with a disorder of the keto-body metabolism.

8. The method of claim 6, wherein the disease is selected among craniocerebral trauma, stroke, hypoxia, cardiovascular diseases, myocardial infarction, refeeding syndrome, anorexia, epilepsy, neurodegenerative diseases, dementia, Alzheimer's disease, Parkinson's disease, multiple sclerosis and amyotrophic lateral sclerosis, fat metabolic diseases, glucose transporter defect (GLUT1 defect), VL-FAOD and mitochondriopathies, mitochondrial thiolase defect, Huntington's disease, cancers, T-cell lymphomas, astrocytomas and glioblastomas, HIV, rheumatic diseases, rheumatoid arthritis and arthritis urica, diseases of the gastrointestinal tract, chronic inflammatory bowel diseases, ulcerative colitis and Crohn's disease, lyosomal storage diseases, sphingolipidosis, Niemann-Pick disease, diabetes mellitus and effects or side-effects of chemotherapy.

9. A food or a food product comprising at least one polyglycerol ester of an acetoacetyl-capped 3-hydroxybutyric acid according to claim 1.

* * * * *